US009718957B2

(12) United States Patent
Chan et al.

(10) Patent No.: US 9,718,957 B2
(45) Date of Patent: Aug. 1, 2017

(54) BIODEGRADABLE ORGANIC RADICAL-FUNCTIONALIZED POLYCARBONATES FOR MEDICAL APPLICATIONS

(71) Applicants: International Business Machines Corporation, Armonk, NY (US); AGENCY FOR SCIENCE, TECHNOLOGY AND RESEARCH, Singapore (SG)

(72) Inventors: Julian M. W. Chan, Fremont, CA (US); James L. Hedrick, Pleasanton, CA (US); Ashlynn L. Z. Lee, Singapore (SG); Rudy J. Wojtecki, San Jose, CA (US); Yi Yan Yang, Singapore (SG)

(73) Assignees: International Business Machines Corporation, Armonk, NY (US); Agency For Science, Technology And Research, Singapore (SG)

( * ) Notice: Subject to any disclaimer, the term of this patent is extended or adjusted under 35 U.S.C. 154(b) by 175 days.

(21) Appl. No.: 14/609,778

(22) Filed: Jan. 30, 2015

(65) Prior Publication Data
US 2016/0220705 A1 Aug. 4, 2016

(51) Int. Cl.
| | |
|---|---|
| *A61K 9/00* | (2006.01) |
| *C08L 69/00* | (2006.01) |
| *C08G 64/02* | (2006.01) |
| *C08G 64/18* | (2006.01) |
| *A61K 49/12* | (2006.01) |
| *A61K 49/20* | (2006.01) |
| *A61K 49/08* | (2006.01) |
| *A61K 49/18* | (2006.01) |

(52) U.S. Cl.
CPC ............ *C08L 69/00* (2013.01); *A61K 49/126* (2013.01); *A61K 49/20* (2013.01); *C08G 64/0241* (2013.01); *C08G 64/183* (2013.01); *A61K 49/085* (2013.01); *A61K 49/1809* (2013.01)

(58) Field of Classification Search
None
See application file for complete search history.

(56) References Cited

U.S. PATENT DOCUMENTS

| | | | |
|---|---|---|---|
| 5,250,672 | A | 10/1993 | Sadler et al. |
| 7,531,615 | B2 | 5/2009 | Davis et al. |
| 7,666,972 | B2 | 2/2010 | Jansen et al. |
| 7,686,997 | B2 | 3/2010 | Agarwal et al. |
| 7,718,755 | B2 | 5/2010 | Chatterjee et al. |
| 8,785,591 | B2 | 7/2014 | Allen et al. |
| 2005/0095197 | A1 | 5/2005 | Tuszynski et al. |
| 2005/0124764 | A1* | 6/2005 | Onoi ................ C08C 19/00 525/242 |
| 2010/0179286 | A1 | 7/2010 | Oda et al. |
| 2014/0220093 | A1 | 8/2014 | Coady et al. |

FOREIGN PATENT DOCUMENTS

JP 2013087256 A 5/2013

OTHER PUBLICATIONS

Feng et al. "Construction of functional aliphatic polycarbonates for biomedical applications", Progress in Polymer Science 37 (2012) pp. 211-236.*
Anderson, et al., "Strategies for the Generation of Molecularly Imprinted Polymeric Nitroxide Catalysts", Organic Letters, 2005, vol. 7, No. 22 4879-4882.
Chen, et al., "In vivo Near-Infrared Fluorescence Imaging of Integrin v 3 in Brain Tumor Xenografts", Cancer Research 64, 8009-8014, Nov. 1, 2004.
Chu, et al., "Novel Biodegradable Functional Amino Acid-based Poly(ester amide) Biomaterials: Design, Synthesis, Property and Biomedical Applications", Journal of Fiber Bioengineering & Informatics 5:1 (2012), pp. 1-31.
Gallez, et al., "Spin Labelled Arabinogalactan as MRI Contrast Agent", Magnetic Resonance Imaging, 1994, vol. 12, pp. 61-69.
Lee, et al., "The use of cholesterol-containing biodegradable block copolymers to exploit hydrophobic interactions for the delivery of anticancer drugs", Biomaterials 33 (2012) 1921-1928.
Pratt, et al. "Tagging alcohols with cyclic carbonate: a versatile equivalent of (meth)acrylate for ring-opening polymerization", Chem. Commun., 2008, 114-116.
Rajca, et al., "Organic Radical Contrast Agents for Magnetic Resonance Imaging", J. Am. Chem. Soc. 2012, 134, 15724-15727.
Sato, et al., "Water-proton relaxivities of DNA oligomers carrying TEMPO radicals", Magn. Reson. Chem. 2008, 46, 1055-1058.
Botkin, "Light Stabilization of Polypropylene: an Independent Perspective", SPE International Polyolefins Conference, Houston Texas, Feb. 25-28, 2007.
Hodgson, et al., "Clarifying the Mechanism of the Denisov Cycle: How do Hindered Amine Light Stabilizers Protect Polymer Coatings from Photo-oxidative Degradation?", Macromolecules 2010, 43, 4573-4583.

* cited by examiner

*Primary Examiner* — James Rogers
(74) *Attorney, Agent, or Firm* — Michael R. Roberts

(57) ABSTRACT

Paramagnetic, amphiphilic, biocompatible polymers were prepared comprising a carbonate repeat unit bearing a paramagnetic organic radical, more specifically a nitroxyl radical. The radical polymers can be produced in one step from a precursor polymer bearing an active ester side chain by treating the precursor polymer with a radical-bearing nucleophile. The precursor polymer can be prepared by organocatalyzed catalyzed ring opening polymerization (ROP) of a cyclic carbonate monomer bearing an active ester side chain. The radical polymers can be non-toxic and partially biodegradable. The radical polymers have utility as contrast enhancing agents in a medical imaging application and/or as therapeutic agents for treating a medical condition. The radical polymers can also serve as carriers for therapeutic agents (e.g., drugs) and/or medical image enhancing agents (e.g., NIRF dyes).

28 Claims, 7 Drawing Sheets

BIODEGRADABLE ORGANIC RADICAL-FUNCTIONALIZED POLYCARBONATES FOR MEDICAL APPLICATIONS

PARTIES TO A JOINT RESEARCH AGREEMENT

This invention was made under a joint research agreement between International Business Machines Corporation and the Agency For Science, Technology and Research.

BACKGROUND

The present invention relates to biodegradable organic radical-functionalized polycarbonates for medical applications, and more specifically, to polycarbonates bearing pendant nitroxide radicals for medical applications.

Magnetic resonance imaging (MRI) is a ubiquitous and non-invasive medical imaging technique that is of critical importance to the diagnosis of various human diseases. Today, the most commonly used MRI contrast agents are gadolinium-based complexes containing the highly paramagnetic Gd3+ ion. While these are generally well-tolerated in the majority of patients, there have nevertheless been reports of side effects including a serious condition known as nephrogenic systemic fibrosis. There has thus been significant interest in developing metal-free contrast agents based on paramagnetic organic radicals.

Rajca, et al., "Organic Radical Contrast Agents for Magnetic Resonance Imaging", J. Am. Chem. Soc (2012), volume 134, pages 15724-15727 disclose a fourth-generation poly(propylenimine) dendrimer peripherally functionalized with hydrophilic poly(ethylene oxide) groups and paramagnetic spirocyclohexyl nitroxide radicals. While this reported ORCA material was found to be an effective contrast agent, its synthesis was multi-step and low yielding. Secondly, the contrast agent is not biodegradable; thus there exists the possibility of accumulation-related toxicity. Finally, the major portion of the contrast agent is composed of poly(propylenimine), which is known to be cytotoxic to human cells.

Therefore, a continuing need exists for biodegradable, non-toxic radical materials for therapeutic and/or diagnostic medical applications.

SUMMARY

Accordingly, a polymer is disclosed, comprising:
a radical repeat unit having a structure according to formula (1):

$$\text{(1)}$$

wherein
$R'$ is monovalent group selected from the group consisting of hydrogen (H—*) and groups comprising 1-5 carbons,
each $R''$ is an independent monovalent group selected from the group consisting of hydrogen (H—*) and methyl (Me-*), and
$W'$ is a monovalent moiety comprising a paramagnetic organic radical, wherein the organic radical comprises an unpaired electron of a carbon, oxygen, nitrogen, and/or sulfur.

Also disclosed is a block polymer of formula (4):

$$\text{(4)}$$

wherein
$n'$ represents the number of ethylene oxide repeat units, and has an average value of about 10 to about 250,
$m'$ represents the number of radical repeat units, and has an average value of 1 to about 100,
each $R'$ is an independent monovalent moiety selected from the group consisting of hydrogen (H—*) and groups comprising 1 to 5 carbons,
each $R''$ is an independent monovalent moiety selected from the group consisting of hydrogen (H—*) and methyl (Me-*),
$X'$ is a divalent linking group selected from the group consisting of oxygen (*—O—*), *—N(H)—*, and sulfur (*—S—*),
each $W'$ is a monovalent moiety comprising a nitroxide radical,
each $Z'$ is a monovalent first end group selected from the group consisting of hydrogen (H—*) and groups comprising 1 or more carbons, and
each $Z''$ is a monovalent second end group selected from the group consisting of hydrogen (H—*) and groups comprising 1 or more carbons.

Also disclosed is a composition comprising water and an above-described block polymer, wherein the composition is suitable for enhancing contrast in a medical imaging application.

Further disclosed is a method, comprising:
forming a first mixture comprising water and an above-described block polymer;
forming a second mixture comprising i) a solvent selected from the group consisting of organic solvents, water, and combinations thereof and ii) a medically useful material;
combining the first mixture and the second mixture, thereby forming a third mixture; and
removing organic solvent from the third mixture, thereby forming a composition comprising particles, the particles comprising the block polymer and the medically useful material bound by non-covalent interactions.

Also disclosed is a method, comprising:
contacting living tissue with an above-described polymer, thereby enhancing contrast in a medical imaging application used to view the tissue and/or administering a medical treatment to the tissue, wherein the polymer is water soluble, non-toxic, biodegradable, and paramagnetic.

The above-described and other features and advantages of the present invention will be appreciated and understood by those skilled in the art from the following detailed description, drawings, and appended claims.

DETAILED DESCRIPTION

Figure 1:
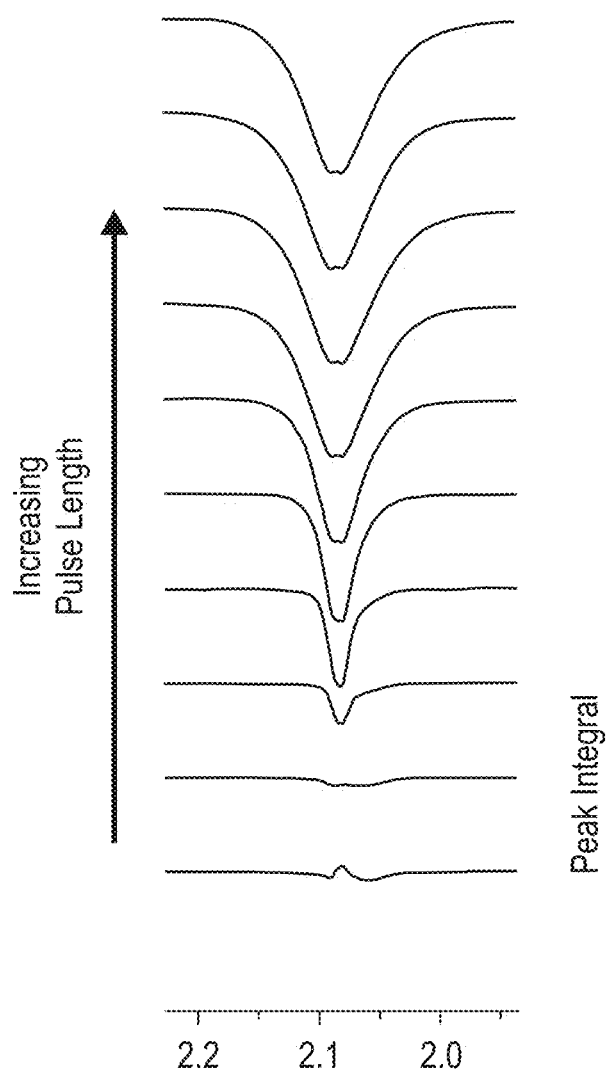
FIG. 1 is a graph of raw $^1$H NMR data where pulse length is incrementally increased during acquisition for radical polymer P1-11 (11 PROXYL units). This is a first step in measuring water relaxation times $T_1$ in magnetic resonance imaging (MRI).

Disclosed are polymers comprising a least one aliphatic carbonate repeat unit comprising a paramagnetic organic radical that has at least one unpaired electron (e.g., a nitroxide radical). These polymers are referred to herein as "radical polymers" or simply "polymers" unless otherwise indicated. The radical polymers can have any suitable architecture. As non-limiting examples, a radical polymer can be a homopolymer, a random copolymer, a block copolymer, a star polymer, a star polymer comprising a cross-linked core, a brush polymer, a dendritic polymer, a mikto-arm polymer, a hydrogel. A given macromolecule of the radical polymer can comprise one or more covalently linked polymer branches. The radical polymers can be anionic, cationic, or non-charged. The radical polymers can be amphiphilic or non-amphiphilic. The radical polymers can be used singularly or in combination. The radical polymers can be soluble in water, an organic solvent, or a mixture thereof. Preferably, the radical polymers form micelles in aqueous solution. In an embodiment, the radical polymers are non-charged, amphiphilic block polymers.

The radical polymers can have utility in medical applications as contrast enhancing agents for medical imaging and/or as therapeutic agents for treating a medical condition (e.g., a disease). The radical polymers can act as carriers for therapeutic agents (e.g., drugs) and/or contrast enhancing agents (e.g., contrast enhancing dyes). In an embodiment, a composition comprises the radical polymer and a contrast enhancing material (e.g., near-infrared fluorescent dye) for medical imaging.

The radical polymers can be non-toxic, biodegradable, and/or biocompatible. The term "biodegradable" is defined by the American Society for Testing and Materials as degradation caused by biological activity, especially by enzymatic action, leading to a significant change in the chemical structure of the material. For purposes herein, a material is "biodegradable" if it undergoes 60% biodegradation within 180 days in accordance with ASTM D6400. Herein, a material is "enzymatically biodegradable" if the material can be degraded (e.g., depolymerized) by a reaction catalyzed by an enzyme.

A "biocompatible" material is defined herein as a material capable of performing with an appropriate host response in a specific application.

Herein, "restricted metals" include ionic and nonionic forms of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table. Metals of Groups 3 to 12 of the Periodic Table include scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, actinium, thorium, protactinium, uranium, neptunium, plutonium, americium, curium, berkelium, californium, einsteinium, fermium, mendelevium, nobelium, lawrencium, rutherfordium, dubnium, seaborgium, bohrium, hassium, meitnerium, darmstadtium, roentgenium, and copernicium. Each one of the foregoing restricted metals can have a concentration in the radical polymer of 0 parts to 100 ppm (parts per million), 0 parts to 100 ppb (parts per billion), or 0 parts to 100 ppt (parts per trillion). Preferably, each one of the foregoing restricted metals has a concentration of 0 parts in the radical polymer (i.e., the concentration is below detection limits). In an embodiment, the chemical formulas of the radical polymers and the components used in the polymerization to prepare the radical polymers contain none of the above restricted metals. A cargo material such as a therapeutic agent and/or a diagnostic enhancing agent, which is carried by the radical polymer, can comprise a restricted metal.

No restriction is placed on the concentration of boron, silicon, or any individual alkali metal of the disclosed radical polymer and/or compositions thereof The amphiphilic radical polymers can be non-cytotoxic. For example, the radical polymers can have a mouse intravenous LD50 value of 200 mg/kg or more. Herein, intravenous LD50 of a substance refers to the median lethal intravenous dosage in milligrams of the substance per kilogram of a test mammal's (e.g., mouse) body mass that kills 50% of the test mammal population in a specified time period.

The carbonate repeat unit comprising the paramagnetic organic radical is referred to hereinafter as a "radical repeat unit". The radical repeat unit has a structure according to formula (1):

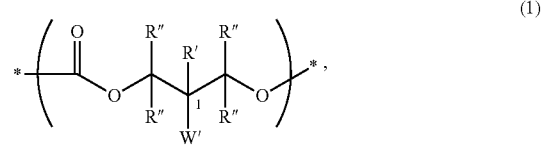

wherein

R' is monovalent group selected from the group consisting of hydrogen (H—*) and groups comprising 1-5 carbons, each R" is an independent monovalent group selected from the group consisting of hydrogen (H—*) and methyl (Me-*), and W' is a monovalent moiety comprising a paramagnetic organic radical, wherein the organic radical comprises an unpaired electron of a carbon, oxygen, nitrogen, and/or sulfur.

Herein, starred bonds represent attachment points, not methyl groups. It should be understood that R' and W' are side chains of the radical repeat unit of the radical polymer which are linked to carbon 1 of the radical polymer backbone. The organic radical moiety is sufficiently stable in aqueous media to have therapeutic use in a medical application. In an embodiment, the organic radical moiety is suitable for an in vivo medical application.

In a preferred embodiment, the paramagnetic organic radical of W' is a nitroxide radical. The divalent nitroxide radical has a structure *—N(—O—)—*, also written as formula (2):

(2)

It should be understood from formula (2) that the unpaired electron can be delocalized over the oxygen and the nitrogen. Each nitrogen starred bond of formula (2) is linked to a different atomic center of W' selected from the group consisting of carbon, hydrogen, oxygen, and sulfur. As non-limiting examples, each starred bond of the nitrogen of formula (2) can be independently linked to an atomic center of W' selected from the group consisting of hydrogen (H—*), alkyl carbon, alkylene carbon, alkyne carbon, methine carbon, oxygen of an alkoxy group (*—OR), sulfur of an alkylthio group (*—SR), nitrogen of an amino group (e.g., *—NH$_2$, *—NHR, *—NR$_2$), carbon of an aromatic ring, sulfur of an alkyl sulfone group (*—S(=O)$_2$R), and oxygen of an ester group (*—OC(=O)R), wherein R in the foregoing groups contains at least one carbon. Preferably, the nitrogen of formula (2) is a member of a ring, more particularly a 5-membered or 6-membered ring.

Especially preferred W' groups comprise a radical moiety selected from the group consisting of

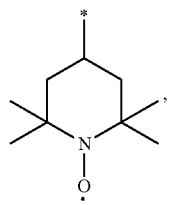 , 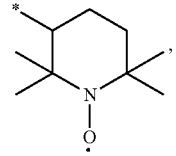 , and (TEMPO-A) (TEMPO-B)

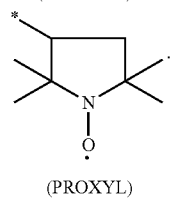

(PROXYL)

The radical polymer can comprise the foregoing radical moieties singularly or in combination.

The radical repeat units comprising TEMPO-A, TEMPO-B, or PROXYL groups have structures according to formula (3);

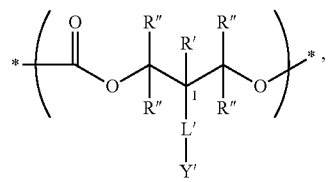

(3)

wherein

R' is monovalent group selected from the group consisting of hydrogen (H—*) and groups comprising 1-5 carbons, each R" is an independent monovalent group selected from the group consisting of hydrogen (H—*) and methyl (Me-*), L' is a divalent linking group selected from the group consisting of a single bond and groups comprising at least one member of the group consisting of carbon, oxygen, sulfur, and nitrogen, and Y' is a radical moiety selected from the group consisting of TEMPO-A, TEMPO-B, and PROXYL.

No restriction is placed on L' with the proviso that the medical utility of the radical polymer is not adversely affected. Exemplary non-limiting L' groups include those of Scheme 1 below, wherein the starred bond of carbon 1, oxygen 1, or nitrogen 1 of the L' group is linked to carbon 1 of formula (3), and the remaining starred bond of the L' group is linked to a TEMPO-A, TEMPO-B, or a PROXYL group.

Scheme 1.

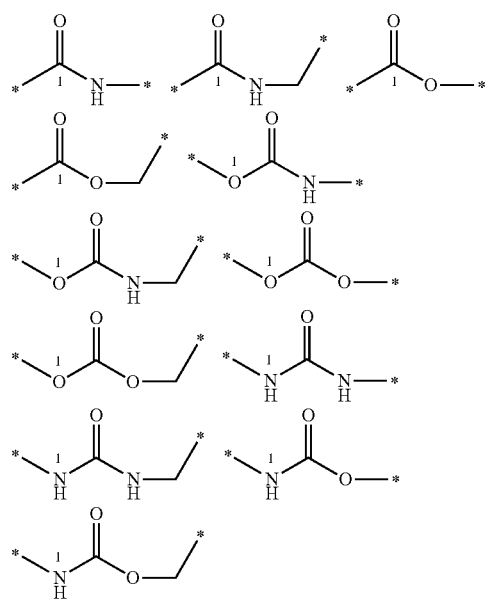

Other non-limiting L' groups will be readily apparent to those skilled in the art. In an embodiment, the L' group comprises 1 to 10 carbons.

Exemplary non-limiting L'-Y' groups (W' groups) include those of Scheme 2, wherein the starred bond of the L'-Y' group is linked to carbon 1 of formula (3).

Scheme 2.
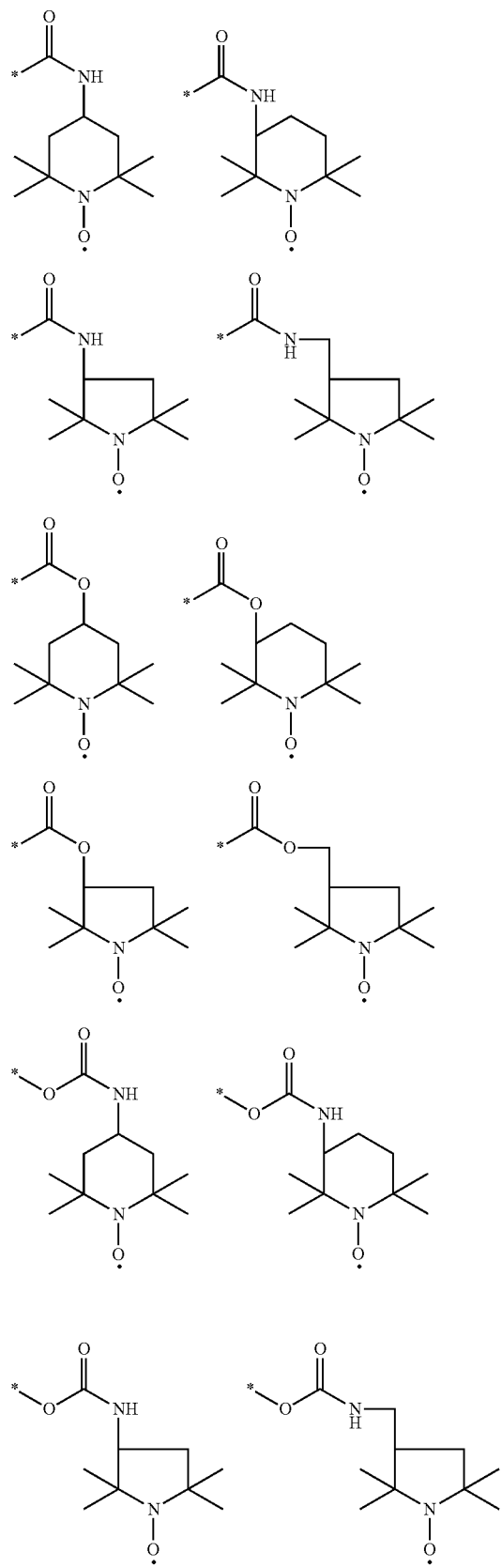
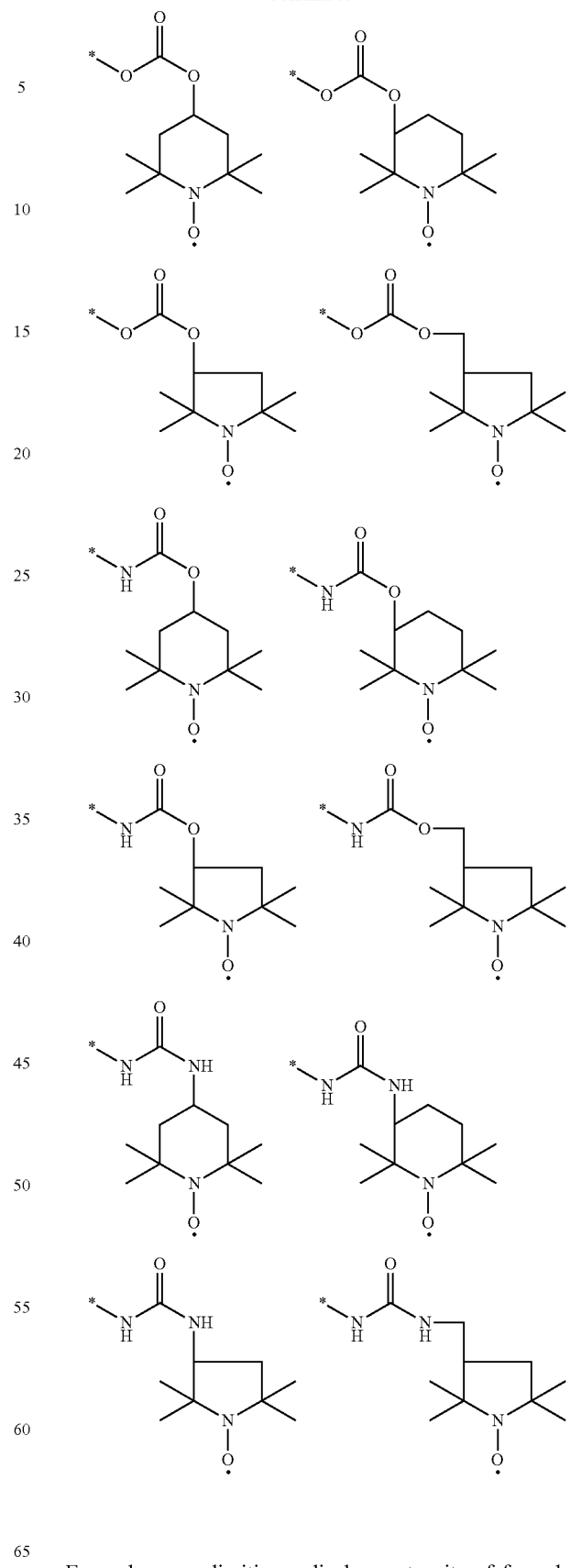
Exemplary non-limiting radical repeat units of formula (1) include those of Scheme 3.

Scheme 3.
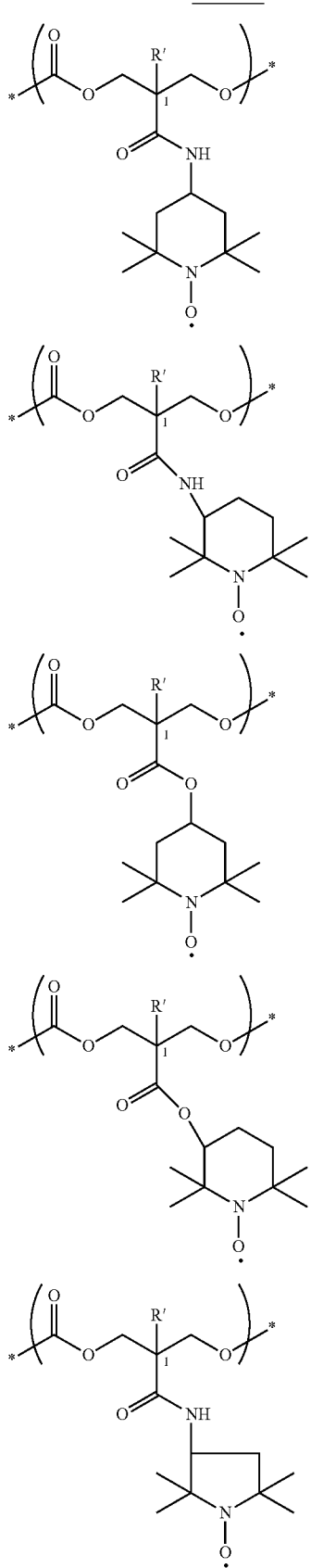
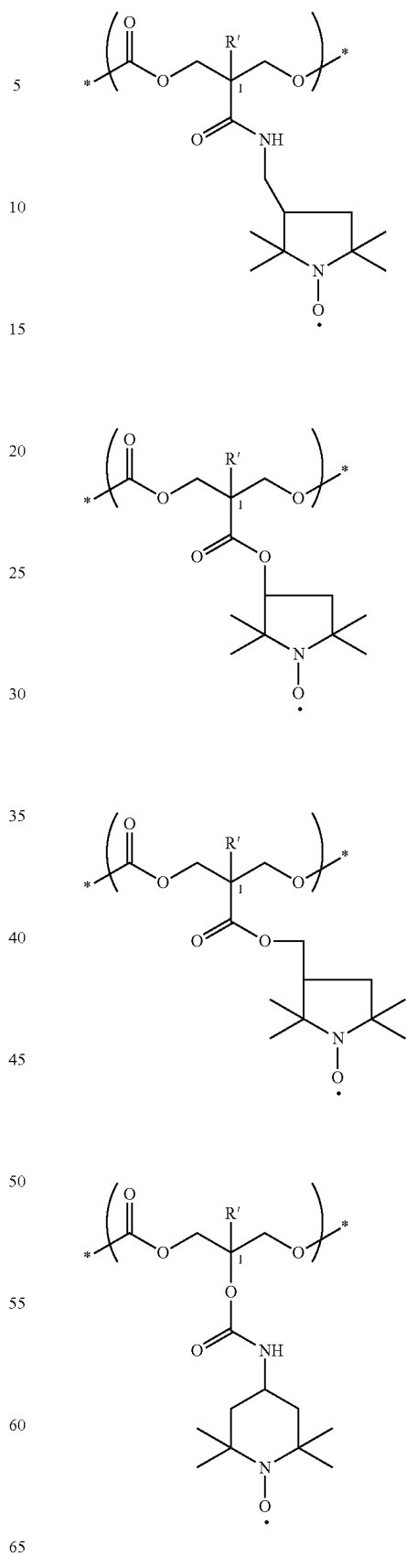

11
-continued
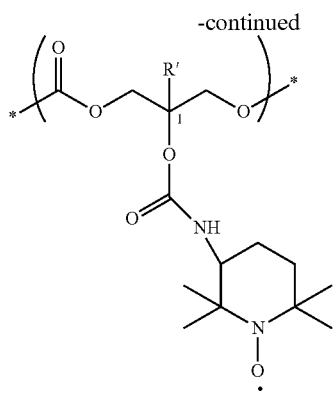
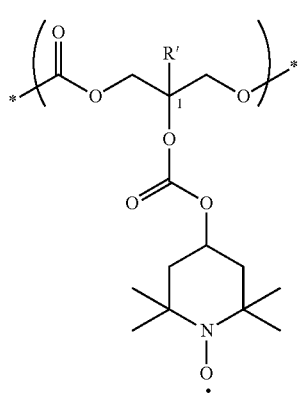
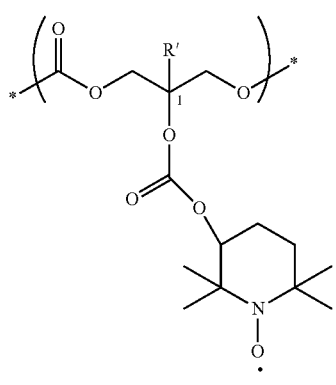
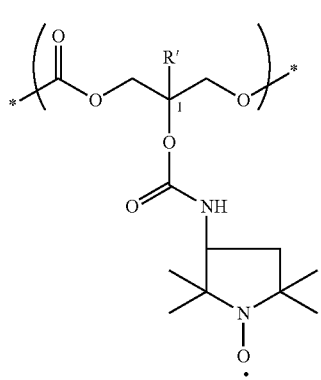
12
-continued
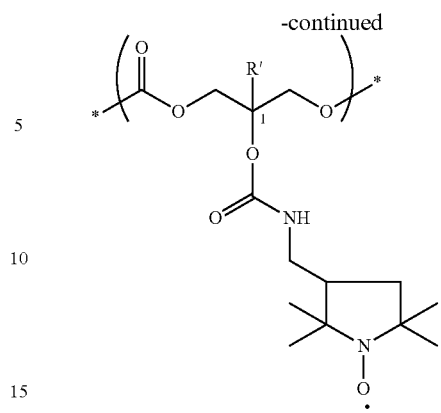
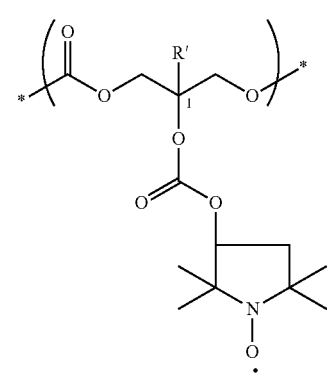
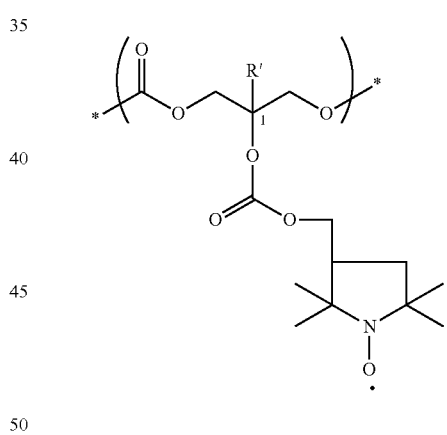
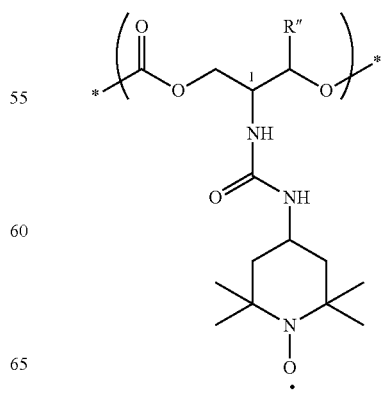

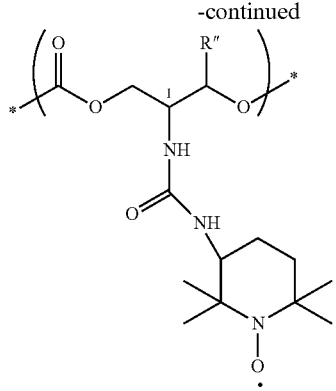

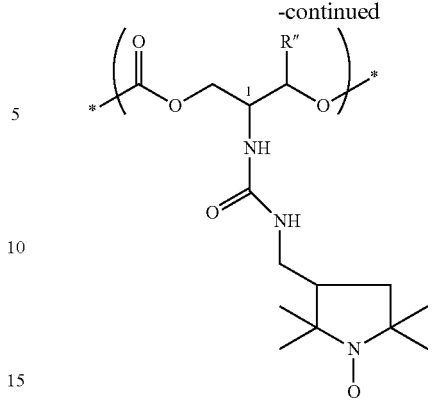

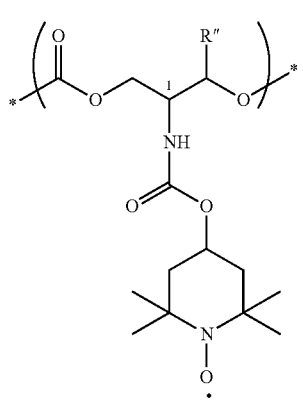

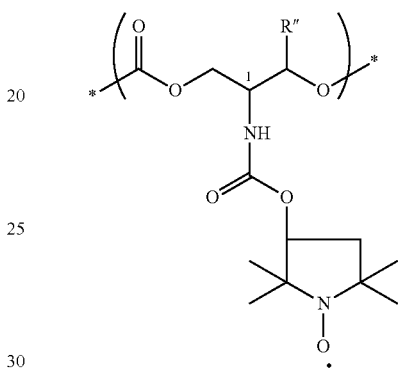

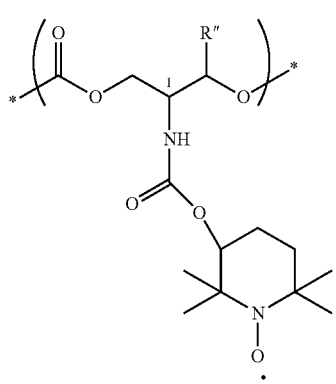

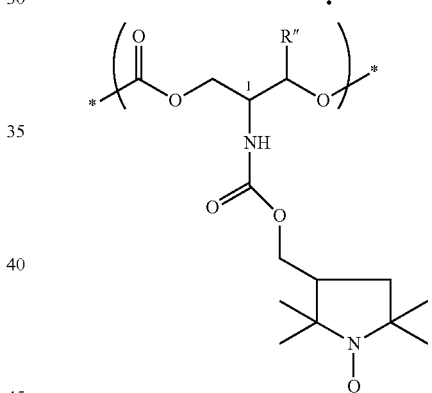

R' = H, Me, Et
R'' = H, Me

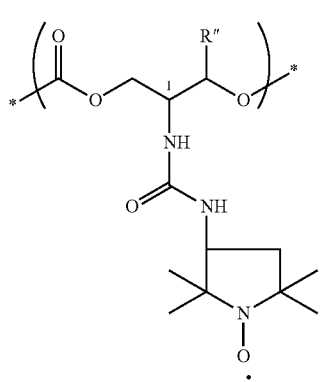

The radical repeat unit can be stereospecific or non-stereospecific.

Radical Polymers

Preferably, the radical polymer is a block copolymer comprising a first block which is hydrophilic and a second block (polycarbonate block) comprising the radical repeat unit. The first block preferably comprises a poly(ethylene oxide) chain that has a number average molecular weight of about 1000 to about 10000, more specifically about 1000 to about 5000. Herein, the first block is also referred to as a "PEG block" due to the repeating units of the first block being the same as those of a polyethylene glycol (PEG).

More specific radical polymers have a structure according to formula (4):

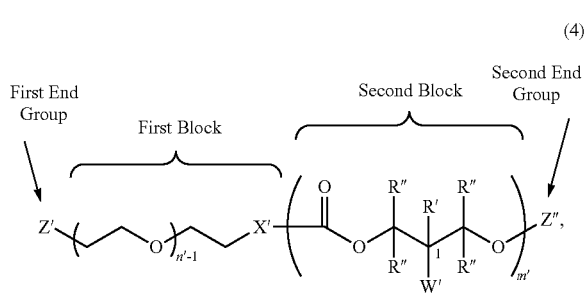

(4)

wherein n' represents the number of ethylene oxide repeat units, and has an average value of about 10 to about 250, m' represents the number of radical repeat units, and has an average value of 1 to about 100, each R' is an independent monovalent moiety selected from the group consisting of hydrogen (H—*) and groups comprising 1 to 5 carbons, each R" is an independent monovalent moiety selected from the group consisting of hydrogen (H—*) and methyl (Me-*), X' is a divalent linking group selected from the group consisting of oxygen (*—O—*), *—N(H)—*, and sulfur (*—S—*), each W' is a monovalent moiety comprising a nitroxide radical, each Z' is a monovalent first end group selected from the group consisting of hydrogen (H—*) and groups comprising 1 or more carbons, and each Z" is a monovalent second end group selected from the group consisting of hydrogen (H—*) and groups comprising 1 or more carbons.

The first end group, first block, second block, and second end group of the radical polymer are labeled in formula (4). In an embodiment, X' is oxygen (*—O—*).

Z' can be any suitable end group. Non-limiting examples of Z' include hydrogen (H—*), hydroxyl group (HO—*), alkoxy group (RO—*), acyloxy group (RC(=O)O—*), amide group (RC(=O)NH—*), thiol group (HS—*), and alkylthio group (RS—*), wherein R in each of the foregoing groups comprises one or more carbons. Z' can comprise one or more functional groups, which include but are not limited to alkyl groups, cycloalkyl groups, ester groups, cyclic ester groups, ketone groups, alcohol groups, alkene groups, alkyne groups, cyloalkyl groups, aromatic groups, amide groups, ether groups, thioether groups, thioester groups, carboxylic acid groups, and any of the foregoing groups substituted with one or more halides such as fluoride, chloride, bromide, and/or iodide. Z' can comprise a biologically active group such as a steroid group (e.g., cholesterol), vitamin group (e.g., vitamin E), monosaccharide group (e.g., mannose), fatty acid group, amino acid group, peptide group, and polypeptide group. In an embodiment, Z' is an alkoxy or aryloxy group comprising 1 to 15 carbons. In an embodiment, Z' is a methoxy group (MeO—*).

Z" can be any suitable end group. Non-limiting examples of Z" include hydrogen (H—*), alkyl (R—*), and acyl (RC(=O)—*) groups, wherein R in the foregoing groups comprises one or more carbons. Z" can comprise one or more functional groups, which include but are not limited to alkyl groups, cycloalkyl groups, ester groups, cyclic ester groups, ketone groups, alcohol groups, alkene groups, alkyne groups, aromatic groups, amide groups, ether groups, carboxylic acid groups, and any of the foregoing groups substituted with one or more halides such as fluoride, chloride, bromide, and/or iodide. Z" can comprise a biologically active group such as a steroid group (e.g., cholesterol), vitamin group (e.g., vitamin E), monosaccharide group (e.g., mannose), fatty acid group, amino acid group, peptide group, and polypeptide group. In an embodiment, Z" is hydrogen (H—*).

In an embodiment, n' has an average value of about 50 to about 200, and m' has an average value of about 1 to about 20. In another embodiment, n' has an average value of about 100 to about 120 and m' has an average value of about 5 to about 15. In another embodiment, the second block consists essentially of the radical repeat unit.

The second block that comprises the radical repeat unit can be biodegradable and biocompatible, which upon its eventual breakdown, leaves only the first block (PEG block) and end group Z'. This does not pose a concern because the PEG block can be readily excreted via renal clearance due to its relatively low molecular weight. Furthermore, polyethylene glycol (PEG) is an FDA-approved polymer that is widely used for drug conjugation, consumer product additives, and other biomaterials.

Other more specific radical polymers have a structure according to formula (5):

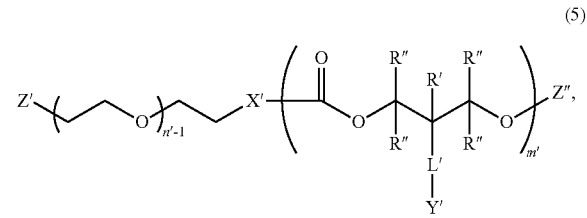

(5)

wherein n' represents the number of ethylene oxide repeat units, and has an average value of about 10 to about 250, m' represents the number of radical repeat units, and has an average value of 1 to about 100, L' is a divalent linking group selected from the group consisting of a single bond and groups comprising at least one member of the group consisting of carbon, oxygen, sulfur, and nitrogen, each R' is an independent monovalent moiety selected from the group consisting of hydrogen (H—*) and groups comprising 1 to 5 carbons, each R" is an independent monovalent moiety selected from the group consisting of hydrogen (H—*) and methyl (Me-*), X' is a divalent linking group selected from the group consisting of oxygen (*—O—*), *—N(H)—*, and sulfur (*—S—*), Y' is a radical moiety selected from the group consisting of TEMPO-A, TEMPO-B, and PROXYL, each Z' is a monovalent first end group selected from the group consisting of hydrogen (H—*) and groups comprising 1 or more carbons, and each Z" is a monovalent second end group selected from the group consisting of hydrogen (H—*) and groups comprising 1 or more carbons.

In an embodiment, X' is oxygen (*—O—*) and Z' is methoxy (MeO—*).

Preparation of Radical Polymers

The radical polymers are preferably prepared from a precursor polymer comprising an active carbonate repeat unit having a structure according to formula (6):

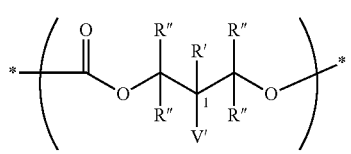

(6)

wherein

R' is monovalent group selected from the group consisting of hydrogen (H—*) and groups comprising 1-5 carbons, each R" is an independent monovalent group selected from the group consisting of hydrogen (H—*) and methyl (Me-*), and V' is a monovalent moiety comprising an electrophilic group capable of undergoing a nucleophilic substitution reaction with a nucleophilic agent comprising a paramagnetic organic radical, wherein the organic radical comprises an unpaired electron of a carbon, oxygen, nitrogen, and/or sulfur.

The active carbonate repeat unit is also referred to herein as "active repeat unit".

V' can comprise any electrophilic group capable of undergoing a substitution reaction with a nucleophilic agent comprising a paramagnetic organic radical. Non-limiting electrophilic groups include active esters, active carbonates, and active carbamates. Non-limiting examples of these are shown below in Scheme 4.

Scheme 4.

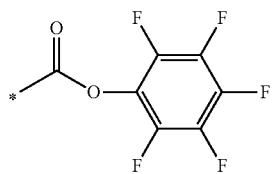
pentafluorophenyl ester

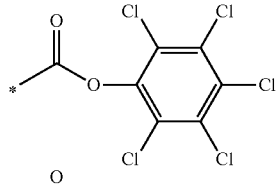

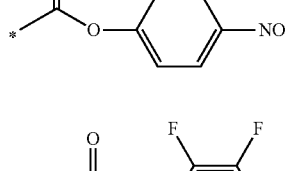

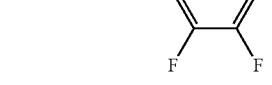
pentafluorophenyl carbonate

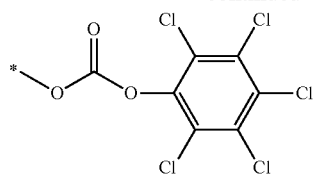

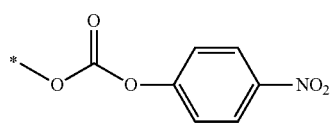

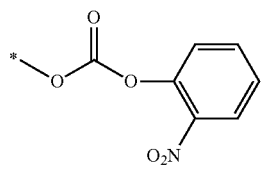

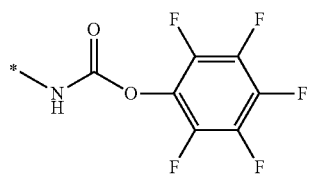
pentafluorophenyl carbamate

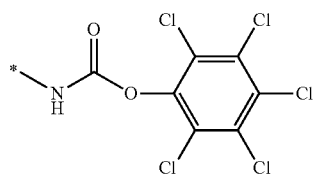

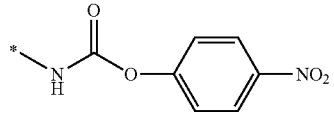

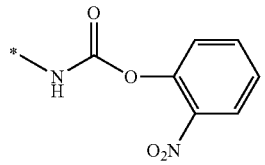

Preferably, V' comprises a member selected from the group consisting of pentafluorophenyl ester group (PFP ester), pentafluorophenyl carbonate (PFP carbonate) group, and pentafluorophenyl carbamate (PFP carbamate) group.

More specific electrophilic repeat units include PFP ester repeat units of formula (7):

PFP carbonate repeat units of formula (8):

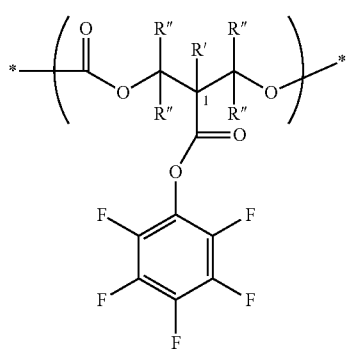
(7)

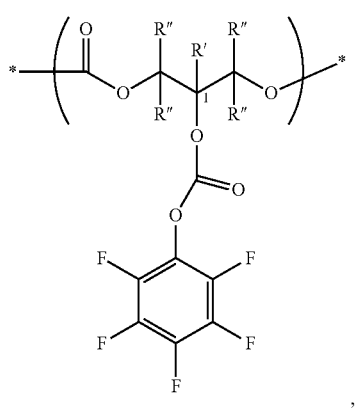
(8)

and
PFP carbamate repeat units of formula (9):

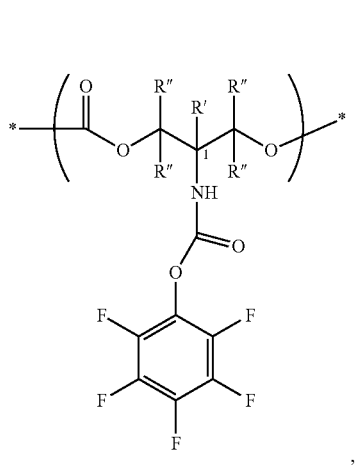
(9)

wherein in each of formulas (7), (8) and (9)
R' is an independent monovalent moiety selected from the group consisting of hydrogen (H—*) and groups comprising 1 to 5 carbons, and
each R" is an independent monovalent moiety selected from the group consisting of hydrogen (H—*) and methyl (Me-*).
Other more specific electrophilic repeat units include PFP ester repeat units of formula (10):

PFP carbonate repeat units of formula (11):

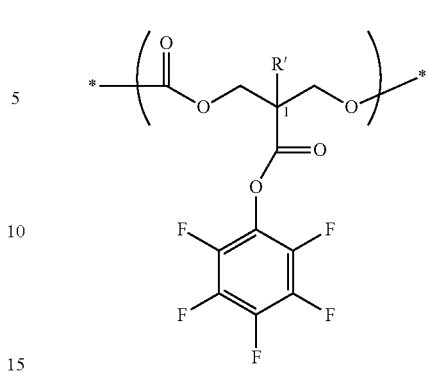
(10)

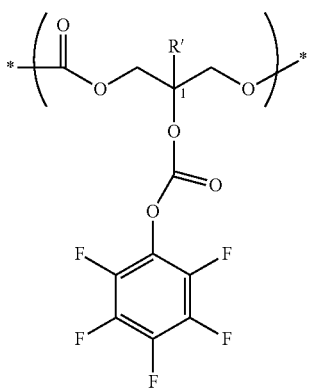
(11)

and
PFP carbamate repeat units of formula (12):

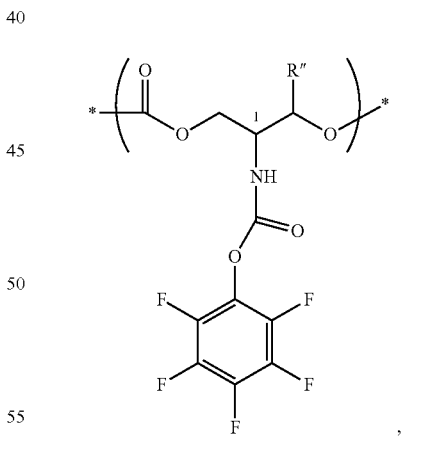
(12)

wherein in each of formulas (10), (11) and (12)
R' is an independent monovalent moiety selected from the group consisting of hydrogen (H—*) and groups comprising 1 to 5 carbons, and
R" is a monovalent moiety selected from the group consisting of hydrogen (H—*) and methyl (Me-*).
Non-limiting examples of nucleophilic agents comprising a paramagnetic organic radical include those of Scheme 5 below. The TEMPO-A, TEMPO-B, and PROXYL moieties are indicated.

Scheme 5.

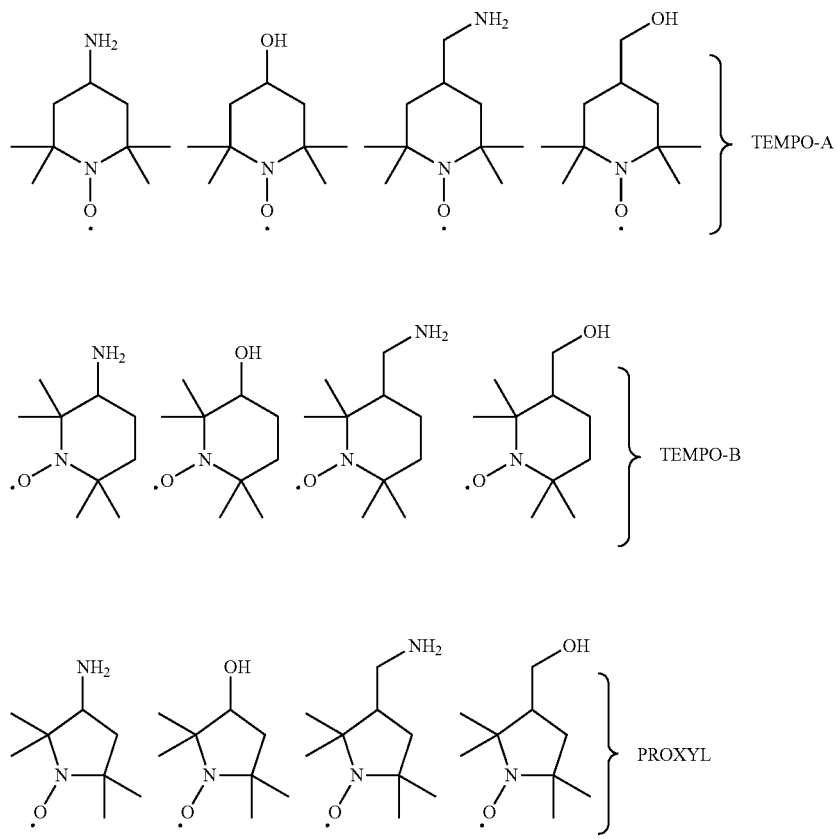

Preferably, the precursor polymer is a block copolymer comprising a hydrophilic first block and a second block (polycarbonate block) that comprises the active repeat unit. The first block preferably comprises a poly(ethylene oxide) chain that has a number average molecular weight of about 1000 to about 10000, more specifically about 1000 to about 5000.

More specific precursor polymers have a structure according to formula (13):

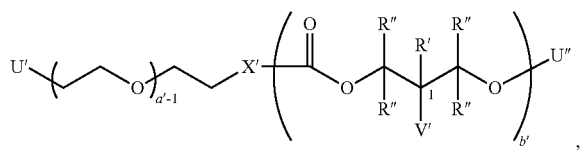

(13)

wherein a' represents number of ethylene oxide repeat units, and has an average value of about 10 to about 250, b' represents number of active repeat units, and has an average value of 1 to about 100, each R' is an independent monovalent moiety selected from the group consisting of hydrogen (H—*) and groups comprising 1 to 5 carbons, each R" is an independent monovalent moiety selected from the group consisting of hydrogen (H—*) and methyl (Me-*), each V' is a monovalent moiety comprising an electrophilic group capable of undergoing a nucleophilic substitution reaction with a nucleophile agent comprising a paramagnetic organic radical, wherein the organic radical comprises an unpaired electron of a carbon, oxygen, nitrogen, and/or sulfur, U' is a monovalent first end group selected from the group consisting of hydrogen (H—*) and groups comprising 1 or more carbons, U" is a monovalent second end group selected from the group consisting of hydrogen (H—*) and groups comprising 1 or more carbons, and X' is a divalent linking group selected from the group consisting of oxygen (*—O—*), *—N(H)—*, and sulfur (*—S—*).

U' can be any suitable end group. Non-limiting examples of U' include hydrogen (H—*), hydroxyl group (HO—*), alkoxy group (RO—*), acyloxy group (RC(=O)O—*), amide group (RC(=O)NH—*), thiol group (HS—*), and alkylthio group (RS—*), wherein R comprises one or more carbons. U' can comprise one or more functional groups selected from the group consisting of alkyl groups, cycloalkyl groups, ester groups, cyclic ester groups, ketone groups, alcohol groups, alkene groups, alkyne groups, cyloalkyl groups, aromatic groups, amide groups, ether groups, thioether groups, thioester groups, carboxylic acid groups, and any of the foregoing groups substituted with one or more halides selected from the group consisting of fluoride, chloride, bromide, and iodide. U' can comprise a biologically active group selected from the group consisting of steroid groups (e.g., cholesterol), vitamin groups (e.g., vitamin E), monosaccharides (e.g., mannose), fatty acids, amino acids, peptides, and polypeptides. In an embodiment, X' is oxygen (*—O—*) and U' is a methoxy group (MeO—*).

U" can be any suitable end group. Non-limiting examples of U" include hydrogen, alkyl (R—*), and acyl (RC(=O)—*), wherein R comprises one or more carbons. U" can comprise one or more functional groups selected from the group consisting of alkyl groups, cycloalkyl groups, ester groups, cyclic ester groups, ketone groups, alcohol groups, alkene groups, alkyne groups, aromatic groups, amide groups, ether groups, carboxylic acid groups, and any of the foregoing groups substituted with one or more halides selected from the group consisting of fluoride, chloride, bromide, and iodide. U" can comprise a biologically active group selected from the group consisting steroid groups (e.g., cholesterol), vitamin groups (e.g., vitamin E), monosaccharides (e.g., mannose), fatty acids, amino acids, peptides, and polypeptides. In an embodiment, U" is hydrogen (H—*).

Preferably a' has an average value of about 100 to about 200, and b' has an average value of about 1 to about 20. In another embodiment, a' has an average value of about 100 to about 120 and b' has an average value of about 5 to about 15. In another embodiment, the second block consists essentially of the activated repeat unit.

Other more specific precursor polymers include those of formula (14):

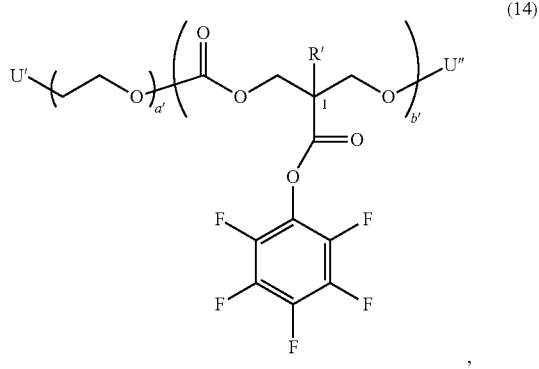

precursor polymers of formula (15):

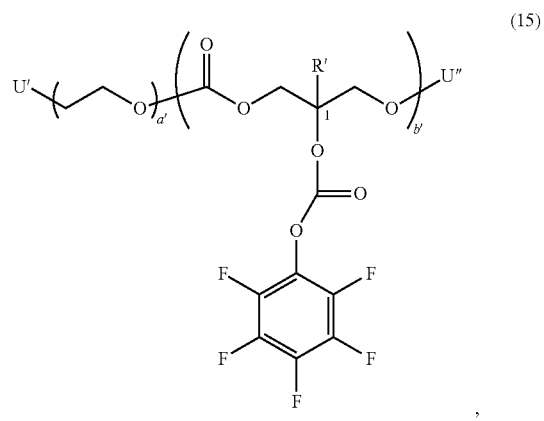

and
precursor polymers of formula (16):

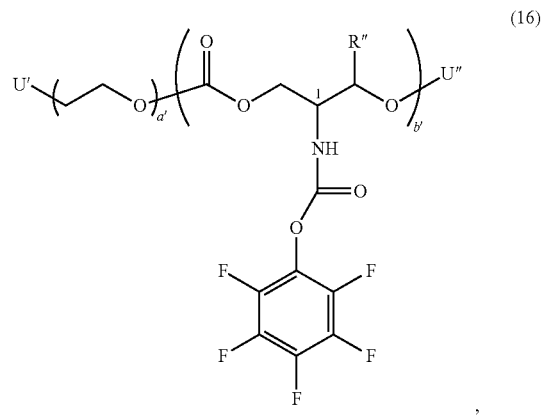

wherein in each of formulas (14), (15) and (16)

a' represents number of ethyleneoxide repeat units, and has an average value of about 10 to about 250, b' represents number of active repeat units, and has an average value of 1 to about 100, R' is an independent monovalent moiety selected from the group consisting of hydrogen (H—*) and groups comprising 1 to 5 carbons, R" is a monovalent moiety selected from the group consisting of hydrogen (H—*) and methyl (Me-*), U' is a monovalent first end group selected from the group consisting of hydrogen (H—*) and groups comprising 1 or more carbons, and U" is a monovalent second end group selected from the group consisting of hydrogen (H—*) and groups comprising 1 or more carbons.

A method of preparing a radical polymer comprises treating a precursor polymer comprising an active carbonate repeat unit of formula (6) with a nucleophilic agent comprising a paramagnetic organic radical, thereby forming the radical polymer. As non-limiting examples, the preparations of radical polymers P1-11 and P2-11 are shown in Scheme 6.

Scheme 6.

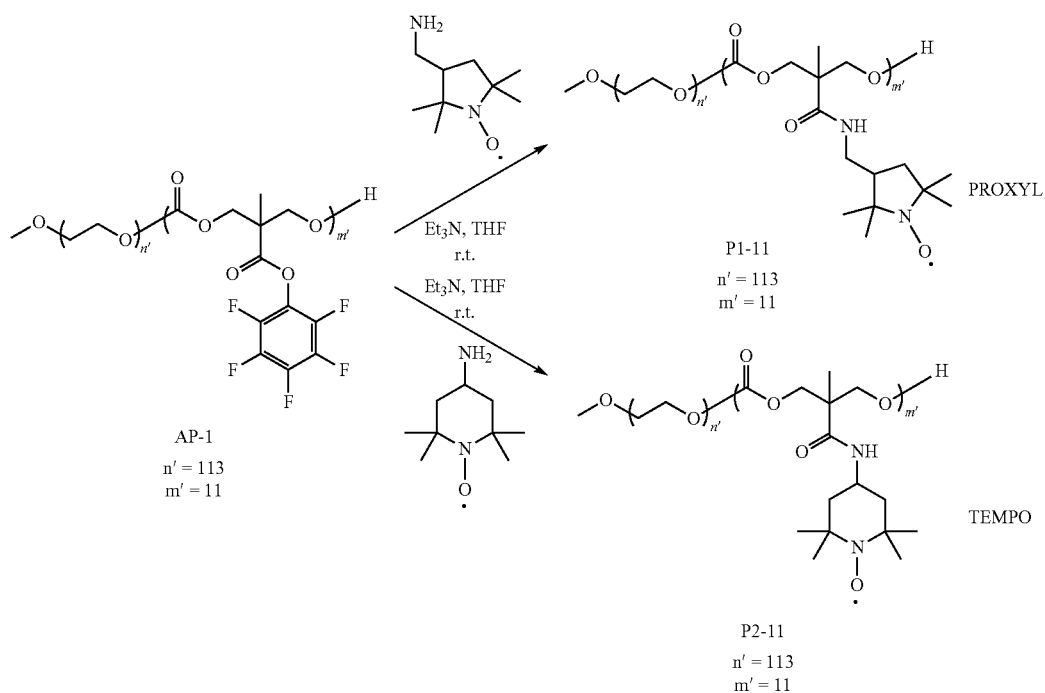

Thus, the commercially available radical moiety can be conveniently introduced in a mild, high yielding, post-polymerization modification step starting from a precursor active polymer (AP-1) comprising pendant pentafluorophenyl ester groups. Optionally, the product radical polymer can be endcapped to prevent back-biting chain scission reactions by the terminal hydroxy group of the polycarbonate chain.

Preparation of Precursor Polymer

The precursor polymer is preferably prepared by an organocatalyzed ring opening polymerization (ROP) of a cyclic carbonate monomer comprising a pendant electrophilic group capable of undergoing a post-ROP nucleophilic substitution reaction with an above-described nucleophilic agent to form the radical polymer. This cyclic carbonate monomer is referred to herein as an "active carbonate monomer".

The active carbonate monomer preferably has a structure according to formula (17):

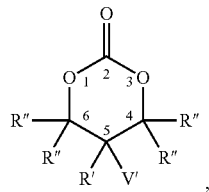

(17)

wherein

R' is monovalent group selected from the group consisting of hydrogen (H—*) and groups comprising 1-5 carbons, each R" is an independent monovalent group selected from the group consisting of hydrogen (H—*) and methyl (Me-*), and V' is a monovalent moiety comprising an electrophilic group capable of undergoing a nucleophilic substitution reaction with a nucleophile agent comprising a paramagnetic organic radical, wherein the organic radical comprises an unpaired electron of a carbon, oxygen, nitrogen, and/or sulfur.

V' has the same definition discussed further above. More specific active carbonate monomers include those formulas (18), (19), and (20) of Scheme 7.

Scheme 7.

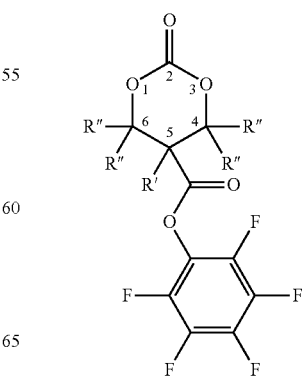

(18)

(19)

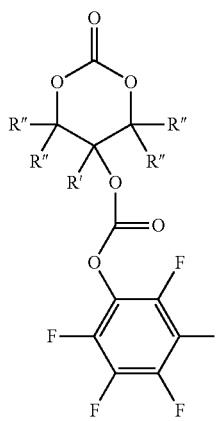

(20)

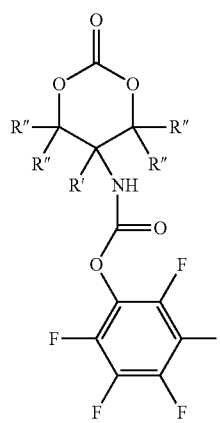

In formulas (18), (19), and (20), R' is an independent monovalent moiety selected from the group consisting of hydrogen (H—*) and groups comprising 1 to 5 carbons, and R" is a monovalent moiety selected from the group consisting of hydrogen (H—*) and methyl (Me-*).

Other more specific active carbonate monomers include the compounds of Scheme 8.

Scheme 8.

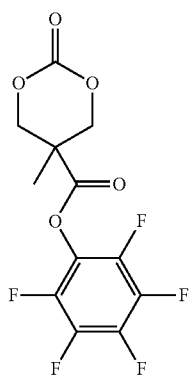
MTC-C6F5

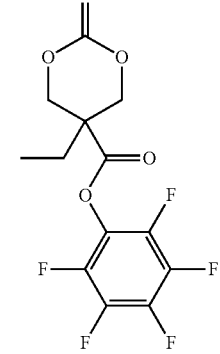

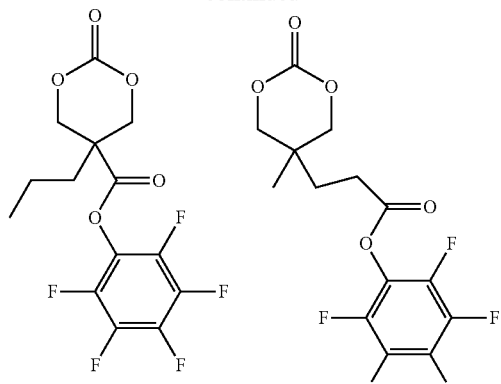

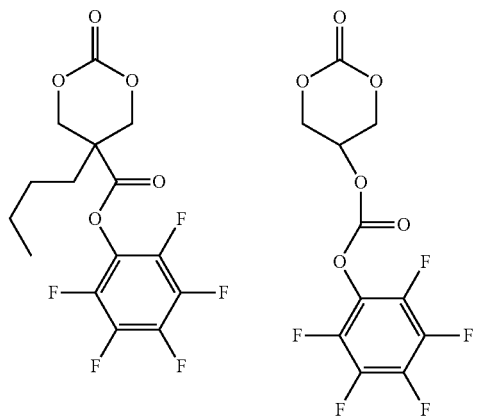

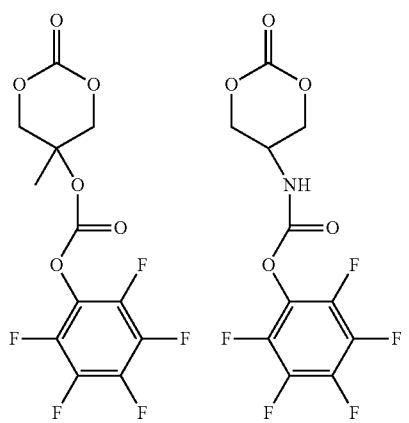

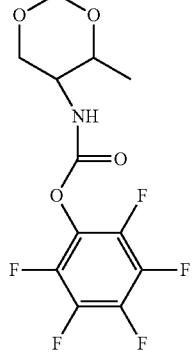

The active carbonate monomer can be stereospecific or non-stereospecific.

The following discussion pertains to active carbonate monomers bearing a pentafluorophenyl ester or a pentafluorophenyl carbonate group. These active carbonate monomers can be prepared by the reaction of a precursor compound (i.e., a diol-carboxylic acid compound or a triol compound, respectively) with bis(pentafluorophenyl) carbonate (PFC):

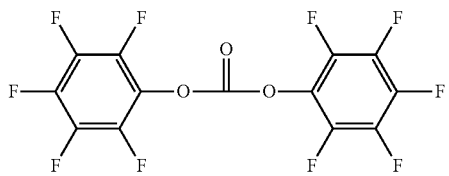

The cyclic carbonyl moiety and the PFP ester or PFP carbonate moiety can be formed in one step by treating a suitable precursor compound with PFC. PFC is less toxic than other reagents used for preparing cyclic carbonyl compounds (e.g., phosgene). PFC is a crystalline solid at room temperature which, being less sensitive to water than phosgene, can be easily stored, shipped, and handled. PFC does not require elaborate reaction and workup conditions. Moreover, the pentafluorophenol byproduct produced during the disclosed cyclization reactions is less volatile, less acidic, and less corrosive than hydrochloric acid. These advantages reduce the cost and complexity of the reactions, and potentially widen the scope of the starting materials to include compounds containing acid-sensitive groups. In addition, the pentafluorophenol byproduct can be readily recycled back into PFC. In an embodiment, the active cyclic monomer formed in the reaction has a single pentafluorophenyl ester group.

The precursor compound can also include isomerically pure forms of the compound or racemic mixtures. The isomerically pure compounds can have an enantiomeric excess of more than 50%, more specifically at least 90%, and even more specifically at least 98%.

Preparation of Active Carbonate Monomers Having a Pendant PFP Ester

A method of preparing an active carbonate monomer comprises forming a mixture comprising bis(pentafluorophenyl) carbonate, a catalyst, an optional solvent, and a precursor compound of formula (21):

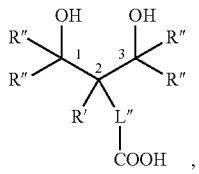

(21)

wherein
L" is a single bond or a linking group comprising 1-10 carbons,
R' is monovalent group selected from the group consisting of hydrogen (H—*) and groups comprising 1-5 carbons, and
  each R" is an independent monovalent group selected from the group consisting of hydrogen (H—*) and methyl (Me-*).

Agitating the mixture produces an active cyclic carbonate monomer of formula (22):

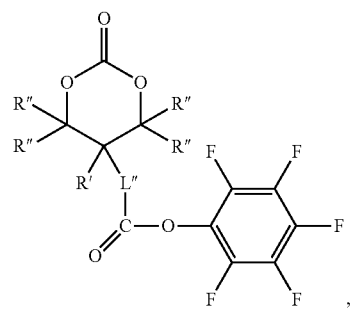

(22)

wherein
L" is a single bond or a linking group comprising 1-10 carbons,
R' is monovalent group selected from the group consisting of hydrogen (H—*) and groups comprising 1-5 carbons, and
  each R" is an independent monovalent group selected from the group consisting of hydrogen (H—*) and methyl (Me-*).

The group

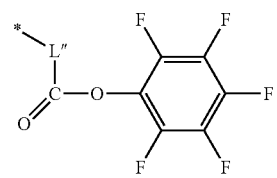

of formula (22) is a member of the group V' of formula (17). In an embodiment, L" is a single bond.

As one example, the preparation of first cyclic monomer MTC-OC6F5 of Scheme 8 can be prepared from a biocompatible precursor compound, bis(2,2-methylol) propionic acid (bis-MPA) as illustrated in Scheme 9.

Scheme 9.

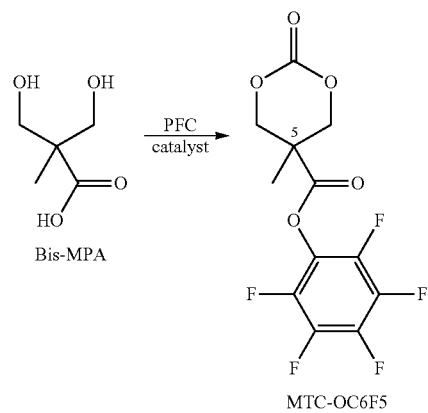

Bis-MPA is converted to MTC-OC6F5 in one step under mild conditions (e.g., at room temperature). MTC-OC6F5 has an active pentafluorophenyl ester (PFP ester) and a methyl group attached to the 5-position of the trimethylene carbonate ring. The reaction can be conducted with about 2 to about 2.5 molar equivalents of PFC, more specifically 2.01 to 2.1 molar equivalents, based on moles of bis-MPA.

Generally, 1 mole of pentafluorophenol is consumed to form the PFP ester and 3 moles of pentafluorophenol are produced as a byproduct (not shown) per 2 moles of PFC used. Each theoretical mole of pentafluorophenol byproduct can be recovered in 90% to 100% yield for recycling back to PFC.

The catalyst can be chosen to activate the nucleophilic diol and not the electrophilic PFC carbonyl group. Exemplary catalysts include tertiary amines, for example, 1,8-bis(dimethylamino)naphthalene, referred to also as PROTON SPONGE, a trademark of Sigma-Aldrich. Still other catalysts include halide salts of Group I elements, particularly lithium (Li), sodium (Na), potassium (K), rubidium (Rb), cesium (Cs), or francium (Fr). In one embodiment the catalyst is CsF.

The catalyst can be present in an amount of 0.02 to 1.00 moles per mole of the precursor compound, more particularly 0.05 to 0.50 moles per mole of the precursor compound, and even more particularly 0.15 to 0.25 moles per mole of the precursor compound.

The reaction mixture generally includes an anhydrous solvent such as tetrahydrofuran, methylene chloride, chloroform, acetone, methyl ethyl ketone, acetonitrile, ethyl acetate, butyl acetate, benzene, toluene, xylene, hexane, petroleum ethers, 1,4-dioxane, diethyl ether, ethylene glycol dimethyl ether, or combinations thereof. The concentration of precursor compound in the solvent can be from about 0.01 to about 10 moles per liter, preferably about 0.02 to 0.8 moles per liter, more preferably 0.1 to 0.6 moles per liter, or more preferably 0.15 to 0.25 moles per liter.

The reaction can be conducted at a temperature from −20° C. to 100° C., 0° C. to 80° C., 10° C. to 50° C., or more preferably ambient or room temperature, typically 17° C. to 30° C. Optionally, the reaction mixture is agitated under an inert atmosphere. In an embodiment, the reaction is conducted at ambient temperature.

The reaction duration can be in the range of about 1 hour to about 120 hours, 5 hours to 48 hours, and more specifically 12 hours to 36 hours. In an embodiment, the reaction is conducted for 15 to 24 hours at ambient temperature.

The resulting reaction mixture comprises the active carbonate monomer comprising the pentafluorophenyl ester and pentafluorophenol byproduct. The active carbonate monomer can be isolated using any known method of purification, including distillation, chromatography, extraction, and precipitation. For example, upon completion of the reaction to form the active carbonate monomer, the solvent can be removed under vacuum followed by addition of a second solvent suitably chosen to selectively precipitate the pentafluorophenol byproduct or the active carbonate monomer. In another variation, the reaction solvent can be selected to facilitate precipitation of the active carbonate monomer or the pentafluorophenol byproduct from the reaction mixture as the reaction proceeds.

Preparation of Active Carbonate Monomers Having a Pendant PFP Carbonate

Another method of preparing an active carbonate monomer comprises forming a mixture comprising bis(pentafluorophenyl) carbonate, a catalyst, an optional solvent, and a precursor compound of formula (23):

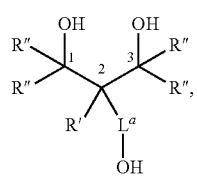

(23)

wherein $L^a$ is a single bond or a linking group comprising 1-10 carbons,

R' is monovalent group selected from the group consisting of hydrogen (H—*) and groups comprising 1-5 carbons, and each R" is an independent monovalent group selected from the group consisting of hydrogen (H—*) and methyl (Me-*).

Agitating the mixture produces an active cyclic carbonate monomer of formula (24):

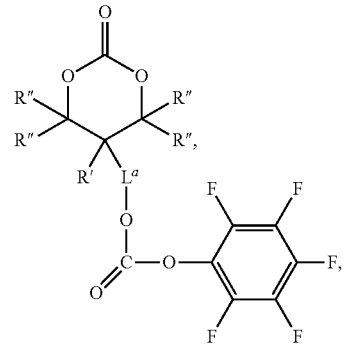

(24)

wherein $L^a$ is a single bond or a linking group comprising 1-10 carbons,

R' is monovalent group selected from the group consisting of hydrogen (H—*) and groups comprising 1-5 carbons, and each R" is an independent monovalent group selected from the group consisting of hydrogen (H—*) and methyl (Me-*).

The group

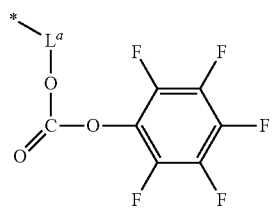

of formula (24) is a member of the group V' of formula (17). In an embodiment, $L^a$ is a single bond.

Ring Opening Polymerization

The following description of ROP methods applies to all cyclic carbonate monomers described herein.

The above-described active carbonate monomers can undergo ring-opening polymerization (ROP) to form biodegradable polymers of different tacticities. Atactic, syndiotactic and isotactic forms of the polymers can be produced that depend on the cyclic carbonate monomer(s), its isomeric purity, and the polymerization conditions.

A method of ring-opening polymerization (ROP) comprises forming a mixture comprising an active carbonate monomer, a catalyst, a polymeric initiator for the ROP, and a solvent. The mixture is heated and agitated to effect polymerization of the active carbonate monomer, thereby forming the precursor polymer comprising the active repeat unit. The precursor polymer has a living end group (hydroxy group) capable of initiating another ROP. Optionally, this end group can be end capped. Treatment of the precursor polymer or the endcapped precursor polymer with an above described nucleophilic agent bearing an organic radical forms the disclosed radical polymer comprising the radical repeat unit of formula (1). Using suitable conditions, the nucleophilic agent can react with the precursor polymer without causing significant cleavage of the precursor polymer backbone.

ROP Catalyst

The ROP reaction mixture includes an organocatalyst whose chemical structure preferably contains none of the restricted metals described further above.

The organocatalyst is preferably an organic acid. Exemplary organic acids include diphenylphosphate, sulfuric acid, p-toluenesulfonic acid, methanesulfonic acid, and trifluoromethane sulfonic acid (triflic acid). In an embodiment, the organocatalyst is trifluoromethane sulfonic acid.

Other organocatalysts for ring opening polymerizations include tertiary amines such as triallylamine, triethylamine, tri-n-octylamine and benzyldimethylamine 4-dimethylaminopyridine, phosphines, N-heterocyclic carbenes (NHC), bifunctional aminothioureas, phosphazenes, amidines, and guanidines.

A more specific organocatalyst is N-bis(3,5-trifluoromethyl)phenyl-N'-cyclohexylthiourea (TU):

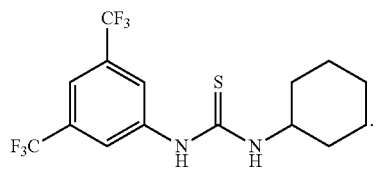

(TU)

Other ROP organocatalysts comprise at least one 1,1,1,3,3,3-hexafluoropropan-2-ol-2-yl (HFP) group. Singly-donating hydrogen bond catalysts have the formula (C-1):

$$R^2\text{---}C(CF_3)_2OH \qquad (C\text{-}1),$$

wherein $R^2$ represents a hydrogen (H—*) or a monovalent group having 1 to 20 carbons, for example an alkyl group, substituted alkyl group, cycloalkyl group, substituted cycloalkyl group, heterocycloalkyl group, substituted heterocycloalklyl group, aryl group, substituted aryl group, or a combination thereof. Exemplary singly-donating hydrogen bonding catalysts are listed in Scheme 10.

Scheme 10.

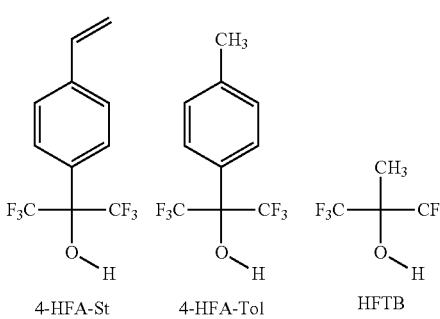

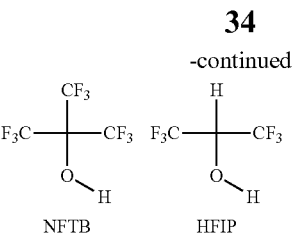

Doubly-donating hydrogen bonding catalysts have two HFP groups, represented by the formula (C-2):

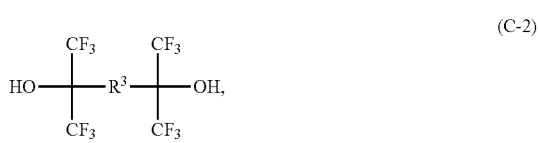

(C-2)

wherein $R^3$ is a divalent radical bridging group comprising 1 to 20 carbons, such as an alkylene group, a substituted alkylene group, a cycloalkylene group, substituted cycloalkylene group, a heterocycloalkylene group, substituted heterocycloalkylene group, an arylene group, a substituted arylene group, or a combination thereof. Representative double hydrogen bonding catalysts of formula (C-2) include those listed in Scheme 11. In a specific embodiment, $R^2$ is an arylene or substituted arylene group, and the HFP groups occupy positions meta to each other on the aromatic ring.

Scheme 11.

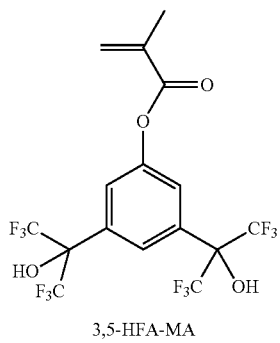

3,5-HFA-MA

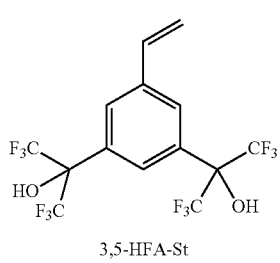

3,5-HFA-St

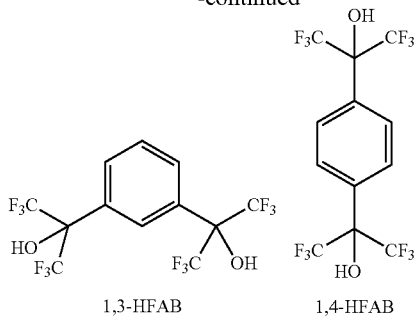

1,3-HFAB      1,4-HFAB

In one embodiment, the catalyst is selected from the group consisting of 4-HFA-St, 4-HFA-Tol, HFTB, NFTB, HPIP, 3,5-HFA-MA, 3,5-HFA-St, 1,3-HFAB, 1,4-HFAB, and combinations thereof Also contemplated are catalysts comprising HFP-containing groups bound to a support. In one embodiment, the support comprises a polymer, a crosslinked polymer bead, an inorganic particle, or a metallic particle. HFP-containing polymers can be formed by known methods including direct polymerization of an HFP-containing monomer (for example, the methacrylate monomer 3,5-HFA-MA or the styryl monomer 3,5-HFA-St). Functional groups in HFP-containing monomers that can undergo direct polymerization (or polymerization with a comonomer) include acrylate, methacrylate, alpha, alpha, alpha-trifluoromethacrylate, alpha-halomethacrylate, acrylamido, methacrylamido, norbornene, vinyl, vinyl ether, and other groups known in the art. Examples of linking groups include $C_1$-$C_{12}$ alkyl, a $C_1$-$C_{12}$ heteroalkyl, ether group, thioether group, amino group, ester group, amide group, or a combination thereof. Also contemplated are catalysts comprising charged HFP-containing groups bound by ionic association to oppositely charged sites on a polymer or a support surface.

The ROP reaction mixture comprises at least one organocatalyst and, when appropriate, several organocatalysts together. The ROP catalyst can be added in a proportion of 1/20 to 1/40,000 moles relative to the cyclic carbonyl monomers, and preferably in a proportion of 1/1,000 to 1/20,000 moles relative to the cyclic carbonyl monomers.

ROP Initiator

The ROP reaction mixture preferably includes a hydrophilic polymeric initiator. The ROP initiator preferably has one nucleophilic group selected from the group consisting of alcohols, amines, and thiols. Preferably, the initiator is a hydrophilic mono-endcapped poly(ethylene glycol) (e.g., mono-methyl poly(ethylene glycol), referred to herein as MPEG). The initiator can have a number average molecular weight (Mn) of about 1000 to about 10000, preferably 1000 to about 5000.

The ROP initiator can have a structure according to formula (I-1):

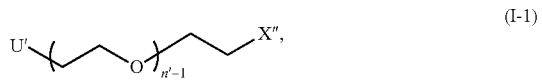

(I-1)

wherein n' has an average value of about 10 to about 250,

U' is a group selected from the group consisting of hydrogen (H—*) and groups comprising 1 or more carbons, X" is a monovalent nucleophilic group selected from the group consisting of *—OH, *—NH$_2$, and *—SH.

In an embodiment, X" is *—OH and U' is methoxy (MeO—*), and n' has an average value of about 100 to about 200.

Diluent Monomers

The ROP reaction mixture can include one or more other cyclic carbonyl monomers selected from the group consisting of cyclic carbonates, cyclic esters, and combinations thereof, which can undergo ring opening to form carbonate or ester repeat units of the radical polymer, respectively. These cyclic carbonyl monomers are referred to herein as diluent monomers and their repeat units are referred to as diluent repeat units. The diluent repeat units can serve to adjust the hydrophilic-hydrophobic balance of the radical polymers. That is, the amphiphilic properties of the radical polymers can be controlled by adjusting the amount and structure of the active carbonate monomer and/or the amount and structure of the diluent repeat units.

More specific diluent cyclic carbonate monomers have a structure according to formula (D-1):

(D-1)

wherein $Q^2$ is a monovalent radical selected from the group consisting of hydrogen (H—*) and alkyl groups comprising 1 to 5 carbons, and $R^3$ is a monovalent radical selected from the group consisting of alkyl groups comprising 1 to 30 carbons and aryl groups comprising 6 to 30 carbons.

The diluent repeat unit formed by ring opening polymerization of the diluent monomer of formula (D-1) has formula (D-2):

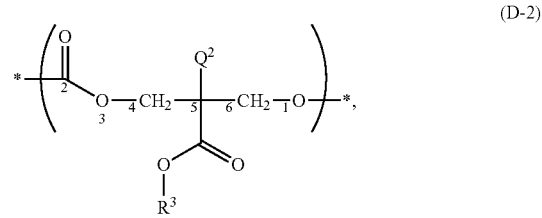

(D-2)

wherein $Q^2$ and $R^3$ are defined as above, and backbone carbons and oxygens are numbered as shown. This diluent repeat unit comprises a backbone carbonate group. In an embodiment, $R^3$ is a group comprising 1 to 6 carbons, and $Q^2$ is methyl (Me-*) or ethyl (Et-*).

Other more specific examples of diluent cyclic carbonate monomers are listed in Scheme 12.

Scheme 12.
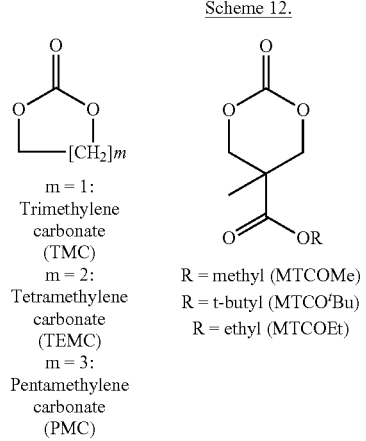
m = 1: Trimethylene carbonate (TMC)
m = 2: Tetramethylene carbonate (TEMC)
m = 3: Pentamethylene carbonate (PMC)
R = methyl (MTCOMe)
R = t-butyl (MTCO$^t$Bu)
R = ethyl (MTCOEt)
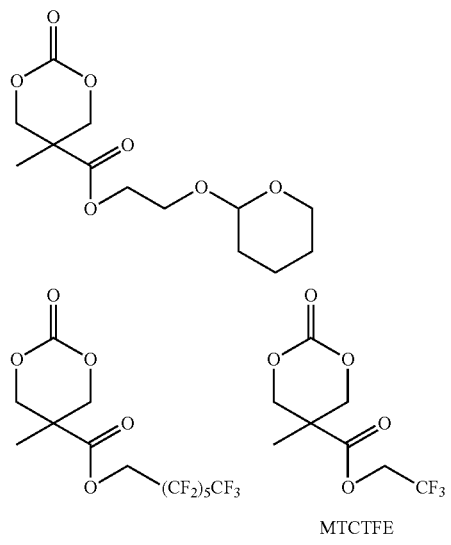
MTCTFE
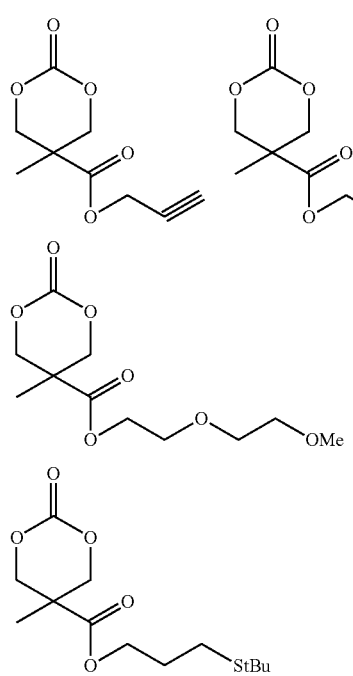
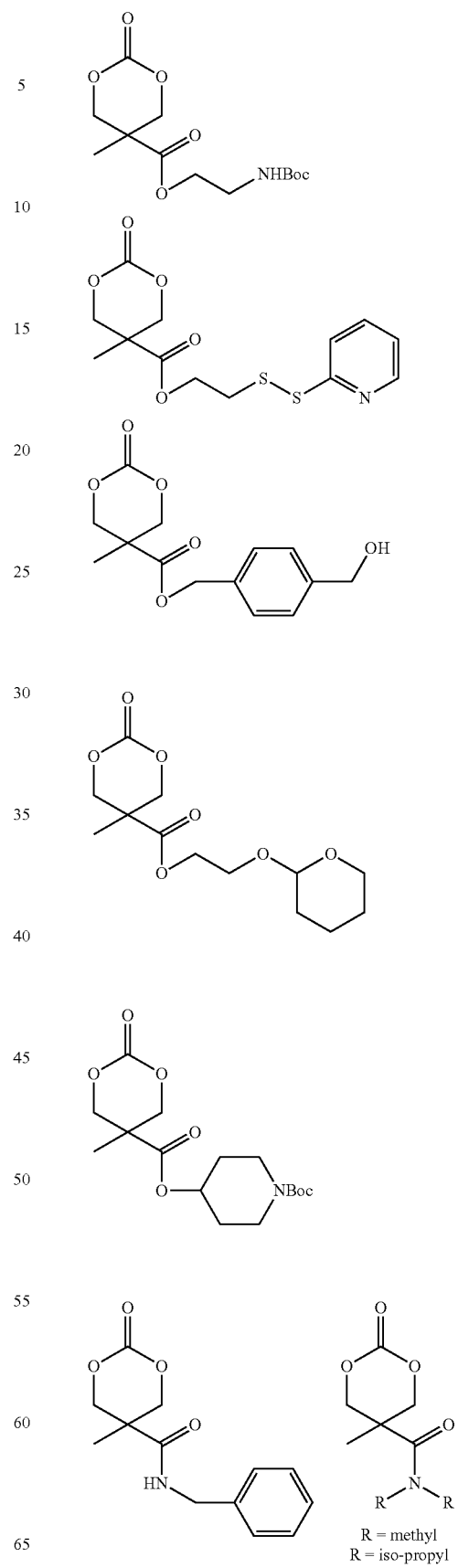
R = methyl
R = iso-propyl

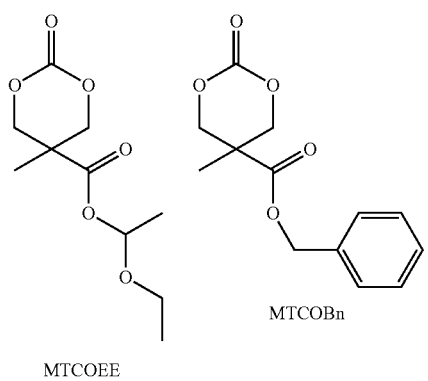

MTCOEE   MTCOBn

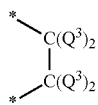

MTCU

Exemplary diluent cyclic ester monomers (e.g., lactones) include compounds of the formula (D-3):

(D-3)

wherein v is an integer of 1 to 8, each $Q^3$ is a monovalent radical independently selected from the group consisting of hydrogen (H—*), alkyl groups comprising 1 to 30 carbons, and aryl groups comprising 6 to 30 carbon atoms. The cyclic ester ring can optionally comprise a carbon-carbon double bond; that is, optionally,

group of formula (D-3) can independently represent a

group. The cyclic ester ring can also comprise a heteroatom such as oxygen, nitrogen, sulfur, or a combination thereof; that is, optionally a

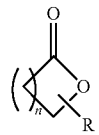

group of formula (D-3) can independently represent a *—O—*, *—S—*, *—N(H)—*, or an *—N($R^1$)—* group, wherein $R^1$ is a monovalent radical independently selected from the group consisting of alkyl groups comprising 1 to 30 carbons and aryl groups comprising 6 to 30 carbons. Cyclic ester monomers of formula (D-3) can be stereospecific or non-stereospecific.

The diluent repeat unit formed by ring opening polymerization of the diluent monomer of formula (D-3) has formula (D-4):

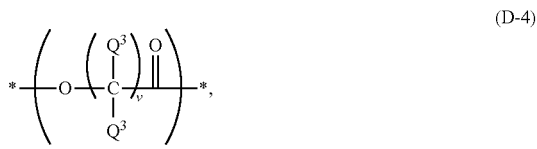

(D-4)

wherein $Q^3$ and v are defined as above under formula (D-3). The diluent repeat unit comprises a backbone ester group.

Other non-limiting examples of diluent cyclic ester monomers include the compounds of Scheme 13 and stereospecific versions thereof where feasible.

Scheme 13.

R = H; n = 1: beta-Propiolactone (b-PL)
R = H; n = 2: gamma-Butyrolactone (g-BL)
R = H; n = 3: delta-Valerolactone (d-VL)
R = H; n = 4: epsilon-Caprolactone (e-CL)
R = $CH_3$; n = 1: beta-Butyrolactone (b-BL)
R = $CH_3$; n = 2: gamma-Valerolactone (g-VL)

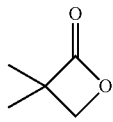 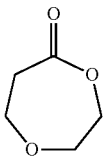

Pivalolactone (PVL)       1,5-Dioxepan-2-one (DXO)

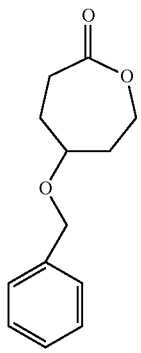

5-(Benzyloxy)
oxepan-2-
one (BXO)

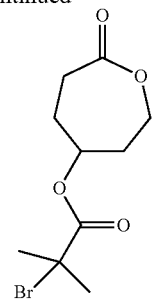

7-Oxooxepan-4-yl 2-bromo-2-
methylpropanoate
(BMP-XO)

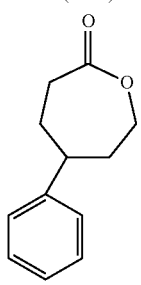

5-Phenyloxepan-
2-one
(PXO)

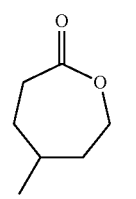

5-Methyloxepan-2-one
(MXO)

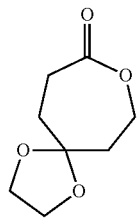

1,4,8-Trioxa(4,6)
spiro-9-
undecane
(TOSUO)

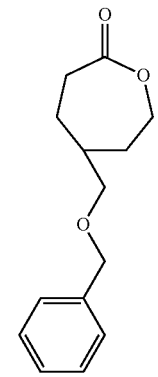

5-(Benzyloxymethyl)oxepan-
2-one (BOMXO)

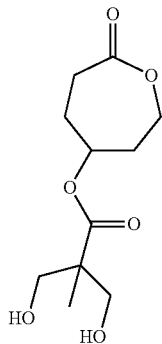

7-Oxooxepan-4-yl
3-hydroxy-2-
(hydroxymethyl)-2-
methylpropanoate
(OX-BHMP)

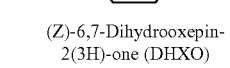

(Z)-6,7-Dihydrooxepin-
2(3H)-one (DHXO)

Other diluent cyclic ester monomers are dioxane dicarbonyl monomers of formula (D-5):

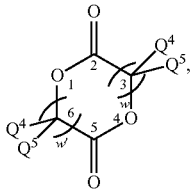
(D-5)

wherein w and w' are independent integers having a value of 1 to 3, and each $Q^4$ and each $Q^5$ is a monovalent radical independently selected from the group consisting of hydrogen (H—*), alkyl groups comprising 1 to 30 carbons, and aryl groups comprising 6 to 30 carbon atoms. Compounds of formula (D-5) can be stereospecific or non-stereospecific. In an embodiment, w and w' are each 1, each $Q^4$ is hydrogen (H—*), and each $Q^5$ is an alkyl group comprising 1 to 6 carbons. In another embodiment, the diluent monomer is D-lactide or L-lactide.

The diluent repeat unit formed by ring opening polymerization of the diluent monomer of formula (D-5) has formula (D-6):

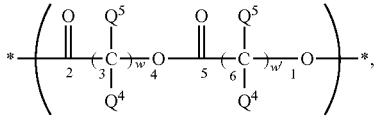
(D-6)

wherein $Q^4$, $Q^5$, w, and w' are defined as above under formula (D-5), and backbone carbons and oxygens are numbered as shown. This second repeat unit has two backbone ester groups.

Examples of diluent monomers of formula (D-5) include the compounds of Scheme 14.

Scheme 14.

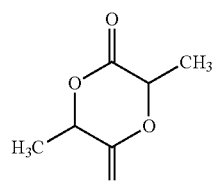

D-Lactide (DLA),
L-Lactide (LLA), or
racemic Lactide, 1:1 D:L forms (DLLA)

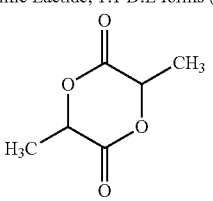

meso-Lactide (MLA)
(two opposite centers of asymmetry,
R and S)

Glycolide (GLY)

The above cyclic carbonyl monomers can be purified by recrystallization from a solvent such as ethyl acetate or by other known methods of purification, with particular attention being paid to removing as much water as possible from the monomer. The monomer moisture content can have a value of 1 to 10,000 ppm, 1 to 1,000 ppm, 1 to 500 ppm, and most specifically 1 to 100 ppm, by weight of the monomer.

Any of the cyclic carbonyl monomers used in the ROP and the repeat units formed therefrom can be stereospecific or non-stereospecific. A stereospecific monomer and/or stereospecific repeat unit i) has a non-superposable mirror image and ii) comprises one or more asymmetric tetravalent carbons (i.e., tetrahedral spa carbons). Each asymmetric tetravalent carbon is assigned an R or S symmetry based on Cahn-Ingold-Prelog (CIP) symmetry rules. For example, if a stereospecific repeat unit has one asymmetric tetravalent carbon, then the stereospecific repeat unit can be present substantially as the R stereoisomer or substantially as the S stereoisomer, meaning the stereoisomer can be present in a stereoisomeric purity of 90% to 100%, 94% or more, or more particularly 98% to 100%. In another example, if the stereospecific repeat unit has two asymmetric tetravalent carbons, the stereospecific repeat unit can be present substantially as the R,R stereoisomer, substantially as the R,S stereoisomer, substantially as the S,S stereoisomer, or substantially as the S,R stereoisomer.

ROP Accelerators

The ROP polymerization can be conducted in the presence of an optional accelerator, in particular a nitrogen base. Exemplary nitrogen base accelerators are listed below and include pyridine (Py), N,N-dimethylaminocyclohexane (Me2NCy), 4-N,N-dimethylaminopyridine (DMAP), trans 1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), 7-methyl-1,5,7-triazabicyclo[4.4.0]dec-5-ene (MTBD), (−)-sparteine, (Sp) 1,3-bis(2-propyl)-4,5-dimethylimidazol-2-ylidene (Im-1), 1,3-bis(2,4,6-trimethylphenyl)imidazol-2-ylidene (Im-2), 1,3-bis(2,6-di-i-propylphenyl(imidazol-2-ylidene (Im-3), 1,3-bis(1-adamantyl)imidazol-2-ylidene (Im-4), 1,3-di-i-propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis(2,6-di-i-propylphenyl)-4,5-dihydroimidazol-2-ylidene, 1,3-bis(2,6-di-i-propylphenyl)-4,5-dihydroimidazol-2-ylidene (Im-8) or a combination thereof, shown in Scheme 15.

Scheme 15.

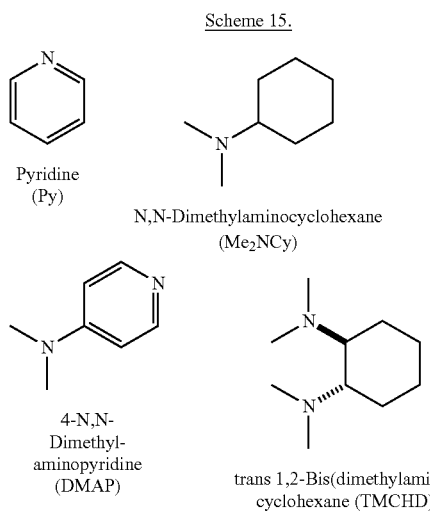

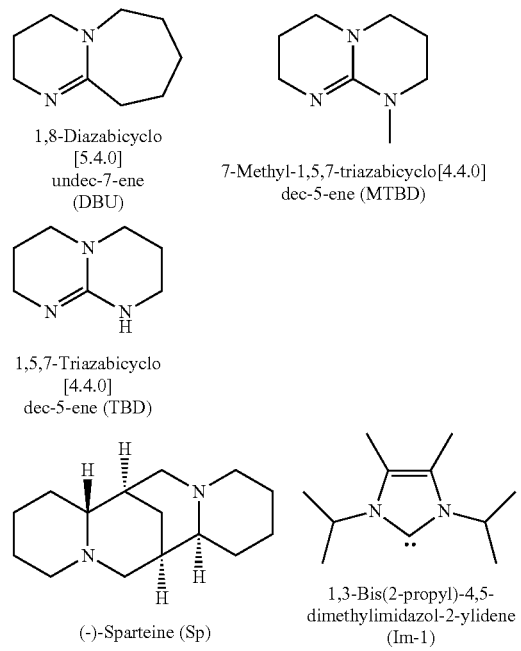

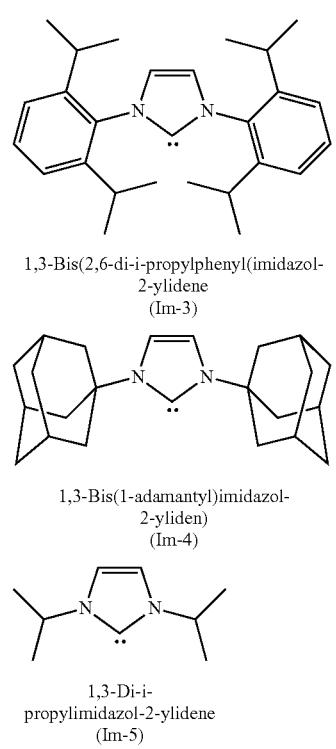

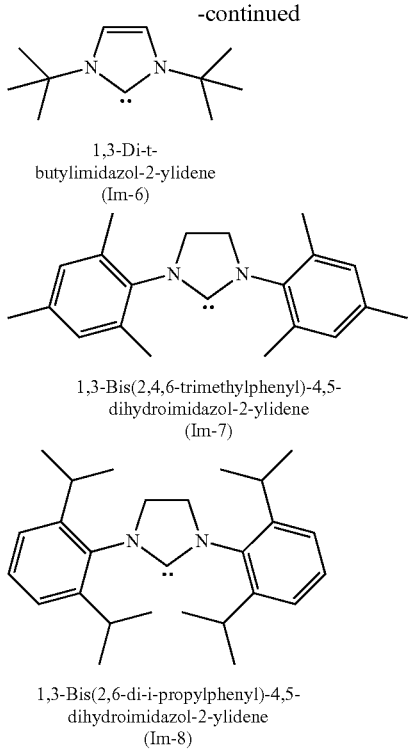

1,3-Di-t-butylimidazol-2-ylidene
(Im-6)

1,3-Bis(2,4,6-trimethylphenyl)-4,5-dihydroimidazol-2-ylidene
(Im-7)

1,3-Bis(2,6-di-i-propylphenyl)-4,5-dihydroimidazol-2-ylidene
(Im-8)

In an embodiment, the accelerator has two or three nitrogens, each capable of participating as a Lewis base, as for example in the structure (−)-sparteine. Stronger bases generally improve the polymerization rate.

ROP Conditions

The ring-opening polymerization is preferably performed at a temperature of about 15° C. to about 50° C., and more preferably 20° C. to 30° C. Reaction times vary with solvent, temperature, agitation rate, pressure, and equipment. In general, the polymerizations are complete within 1 to 100 hours.

The ROP reaction is preferably performed with a solvent. Exemplary solvents include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. A suitable monomer concentration is about 0.1 to 5 moles per liter, and more particularly about 0.2 to 4 moles per liter.

The ROP polymerizations are conducted using a dry, inert atmosphere, such as nitrogen or argon, and at a pressure of 100 MPa to 500 MPa (1 atm to 5 atm), more typically at a pressure of 100 MPa to 200 MPa (1 atm to 2 atm). At the completion of the reaction, the solvent can be removed using reduced pressure.

The catalyst and the accelerator can be the same material. For example, some ring opening polymerizations can be conducted using 1,8-diazabicyclo[5.4.0]undec-7-ene (DBU) alone, with no another catalyst or accelerator present.

The catalyst is preferably present in an amount of about 0.2 to 20 mol %, 0.5 to 10 mol %, 1 to 5 mol %, or 1 to 2.5 mol %, based on total moles of cyclic carbonyl monomer(s) used.

The nitrogen base accelerator, when used, is preferably present in an amount of 0.1 to 5.0 mol %, 0.1 to 2.5 mol %, 0.1 to 1.0 mol %, or 0.2 to 0.5 mol %, based on total moles of cyclic carbonyl monomer. As stated above, in some instances the catalyst and the nitrogen base accelerator can be the same compound, depending on the particular cyclic carbonyl monomer used.

The amount of initiator is calculated based on the equivalent molecular weight per nucleophilic initiator group. The initiator groups are preferably present in an amount of 0.001 to 10.0 mol %, 0.1 to 2.5 mol %, 0.1 to 1.0 mol %, and 0.2 to 0.5 mol %, based on total moles of cyclic carbonyl monomer(s). For example, if the molecular weight of the initiator is 100 g/mole and the initiator has 2 hydroxyl groups, the equivalent molecular weight per hydroxyl group is 50 g/mole. If the polymerization calls for 5 mol % hydroxyl groups per mole of cyclic carbonyl monomer, the amount of initiator is 0.05×50=2.5 g per mole of cyclic carbonyl monomer.

The catalysts can be removed by selective precipitation or in the case of the solid supported catalysts, simply by filtration. The radical polymer can comprise residual catalyst in an amount greater than or equal to 0 wt % (weight percent), based on total weight of the radical polymer and the residual catalyst.

Average Molecular Weight

The radical polymers preferably have a number average molecular weight Mn of about 1000 or more, more preferably about 1000 to about 50,000, and most preferably about 1000 to about 20,000. In an embodiment, the hydrophilic polymer has a number average molecular weight Mn of about 5000 to about 20,000.

The radical polymers can have a polydispersity index (PDI) of 1.01 to 2.0, more preferably 1.01 to 1.30, and even more preferably 1.01 to 1.25.

Endcap Agents

The precursor polymer and/or the radical polymer can further be treated with an endcap agent to prevent further chain growth and stabilize the reactive end groups against unwanted side reactions such as chain scission. Endcap agents include, for example, materials for converting terminal hydroxyl groups to esters, such as carboxylic acid anhydrides, carboxylic acid chlorides, or reactive esters (e.g., p-nitrophenyl esters). In an embodiment, the endcap agent is acetic anhydride, which converts reactive hydroxy end groups to acetate ester groups. The endcap agent can also comprise a biologically active moiety, which becomes bound to the terminal end group of the ring opened polymer chain.

In an embodiment, the radical polymer has a living end group (i.e., not endcapped), which is capable of initiating a ring opening polymerization.

Medical Utility

Disclosed are compositions comprising water and a radical polymer. The compositions can have utility as contrast enhancing agents for medical imaging (e.g., magnetic resonance imaging). The aqueous mixture can have any non-toxic concentration of radical polymer that is suitable for its intended use. The compositions can comprise self-assembled micelles of the radical polymers.

The compositions can further comprise a medically useful cargo material (e.g., a drug and/or a diagnostic agent). The radical polymer can serve as a carrier for the cargo material, which can be bound to the radical polymer by non-covalent interactions (e.g., hydrogen bonding, hydrophobic interactions). The radical polymer can also serve as a dispersing aid for cargo material in an aqueous mixture. Compositions comprising a radical polymer and medically useful cargo material are referred to herein as "loaded polymers".

The loaded polymers can release the cargo material in the blood stream and/or within a cell.

The loaded polymers can be in the form of water-dispersible particles. The particles can have an average particle size as measured by dynamic light scattering of about 10 nm to about 500 nm, more preferably about 10 nm to about 200 nm. The particles can further comprise water.

The loaded polymers can comprise the cargo material in an amount greater than 0 weight percent (wt %), and more particularly in an amount of about 0.1 wt. % to about 15 wt % based on total dry weight of the compositions.

The cargo material can be any suitable medically useful material capable of forming a reversible complex (i.e., by non-covalent interactions) with a disclosed radical polymer, wherein the complex and/or adduct is capable of controlled release of the cargo material. Non-limiting cargo materials include medical therapeutic agents including DNA, genes, peptides, proteins, enzymes, lipids, phospholipids, and nucleotides), natural or synthetic organic compounds (e.g., drugs, dyes, synthetic polymers, oligomers, and amino acids), inorganic materials (e.g., metals and metal oxides), radioactive variants of the foregoing, and combinations of the foregoing. In an embodiment, the cargo material is a drug and/or a gene. In another embodiment, the cargo material is a near infrared fluorescent (NIRF) dye useful for contrast enhancement in a medical imaging application (e.g., magnetic resonance imaging). A NIRF dye fluoresces at a wavelength in a range of about 700 nm to about 900 nm.

The therapeutic agent is effective in inducing a desirable medical response. Non-limiting desirable medical responses include selective alteration of the chemical structure and/or activity of a cell type relative to another cell type. As an example, one desirable change in a chemical structure can be the incorporation of a gene into the DNA of a cell. A desirable change in activity can be the expression of the transfected gene by the cell. Another desirable change in cell activity can be the induced production of a desired hormone or enzyme. Alternatively, a desirable change in activity can be the selective death of one cell type over another cell type. For example, the therapeutic agent can selectively kill a bacterium, inactivate a virus, and/or kill tumor cells. No limitation is placed on the relative change in cellular activity caused by the therapeutic agent, providing the change is desirable and useful. Moreover, no limitation is placed on the therapeutic agent, providing the therapeutic agent induces a medically useful response.

Non-limiting exemplary commercially available drugs include 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cyclosporin (an immunosuppressive agent, normally given to patients for life long after organ transplantation), Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone Acetate, Dexamethasone Sodium Phosphate Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Finasteride (for hair growth), Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, Gemzar, Gleevec™, Gliadel® Wafer, GM-CSF, Goserelin, Granulocyte-Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan Idamycin®, Idarubicin, Ifex®, IFN-alpha Ifosfamide, IL-11 IL-2 Imatinib mesylate, Imidazole Carboxamide Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, K Kidrolase (t), Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Orapred®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a) Rubex®, Rubidomycin hydrochloride, Sandostatin®, Sandostatin LAR®, Sargramostim, Solu-Cortef®, Solu-Medrol®, Sorafenib, SPRYCEL™, Spironolactone, STI-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, and Zometa.

Non-limiting examples of rigid hydrophobic drugs (with stereochemistry shown) include the anti-tumor drug paclitaxel (PTX):

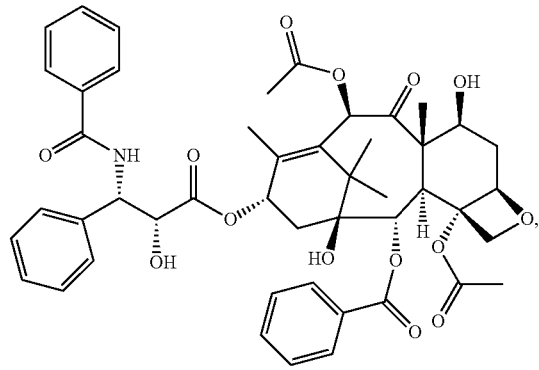 [SMILES: CC(=O)O[C@H]1C(=O)[C@@]2(C)[C@H]([C@H](OC(=O)c3ccccc3)[C@]3(O)C[C@H](OC(=O)[C@H](O)[C@@H](NC(=O)c4ccccc4)c4ccccc4)C(C)=C1C3(C)C)[C@]1(OC(C)=O)CO[C@@H]1C[C@@H]2O]

anti-tumor drug doxorubicin (DOX):

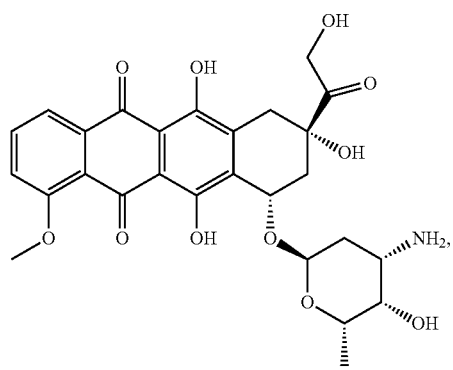 [SMILES: COc1cccc2c1C(=O)c1c(O)c3c(c(O)c1C2=O)C[C@@](O)(C(=O)CO)C[C@@H]3O[C@H]1C[C@H](N)[C@H](O)[C@H](C)O1]

immunosuppressive drug cyclosporin A (CYC):

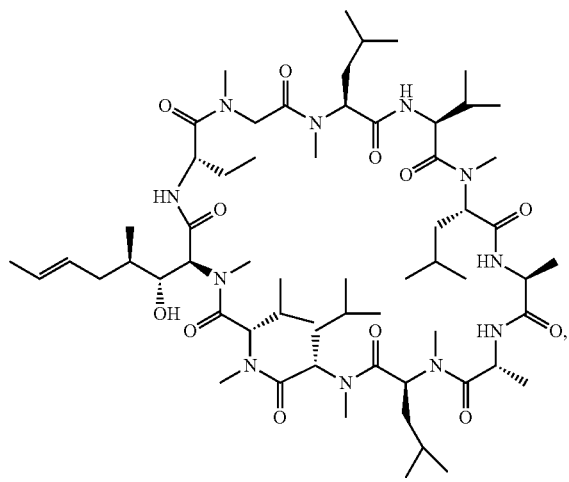 [SMILES: C/C=C/C[C@@H](C)[C@@H](O)[C@H]1C(=O)NCC[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

and
hair growth drug spironolactone (SPL):

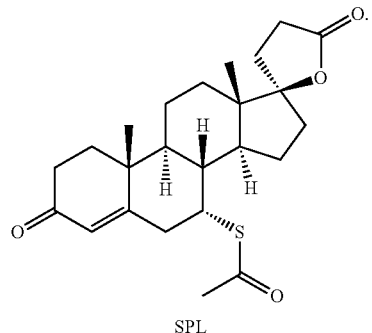

SPL

The therapeutic agents can be used singularly or in combination.

Also disclosed is a method of forming a loaded polymer, comprising i) forming a first mixture comprising water and a disclosed radical polymer, ii) forming a second mixture comprising a medically useful material (e.g., drug, contrast enhancing agent) and a solvent selected from the group consisting of organic solvents, water, and combinations thereof, iii) combining the first mixture and the second mixture, thereby forming a third mixture, and iv) removing the organic solvent(s) from the third mixture, thereby forming the loaded polymer as particles comprising the radical polymer and the medically useful material bound by non-covalent. The particles can have the form of micelles of the radical polymer, which contain the cargo material.

The third mixture can be dialyzed against deionized water using a dialysis membrane system to remove the organic solvent.

Exemplary organic solvents include methanol, ethanol, propanol, 2-propanol, 1-butanol, 2-butanol, t-butyl alcohol, acetone, 2-butanone, dimethoxyethane, diglyme, diethyl ether, methyl t-butyl ether, methylene chloride, ethyl acetate, ethylene glycol, glycerin, dimethylsulfoxide, dimethylformamide, acetic acid, tetrahydrofuran (THF), and dioxane.

The loaded polymer can comprise the radical polymer in an amount of about 50.0 wt % to about 99.9 wt %, and the therapeutic agent in an amount of about 50.0 wt % to about 0.1 wt %, each based on total dry weight of the loaded polymer.

Particles of the loaded polymer can have an average particle size (circular cross sectional diameter) of 10 nm to 500 nm, more preferably 10 nm to 250 nm, and most preferably 25 nm to 200 nm as measured by dynamic light scattering. For the foregoing particle sizes, the aqueous solution can have a pH of 4.5 to 8.0, more particularly 5.0 to 8.0, or even more particularly 7.0 to 8.0.

Living tissue can be contacted in vivo and/or ex vivo with the radical polymers and/or loaded polymers, for the purpose of enhancing contrast in a medical imaging application used to view the tissue and/or administering a medical treatment to the tissue. Preferably the radical polymer is water soluble, non-toxic, biodegradable, and paramagnetic. In another embodiment, the radical polymer is administered to a medical patient. Non-limiting methods of administration of the radical polymers include intravenous injection, oral administration (e.g., liquid, pill), inhalation spray, and combinations thereof.

The following examples illustrate the preparation and properties of the radical polymers and their utility in enhancing contrast in magnetic resonance images.

EXAMPLES

Materials used in the following examples are listed in Table 1.

TABLE 1

| ABBREVIATION | DESCRIPTION | SUPPLIER |
|---|---|---|
| MPEG-5k | Monomethyl Endcapped Poly(ethylene glycol) (PEG); Mn 5000. | Fluka |
| 3-(aminomethyl)-PROXYL | 3-(Aminomethyl)-2,2,5,5-Tetramethyl-1-Pyrrolidinyloxy, free radical (MW 171.26) | Sigma-Aldrich |
| 4-amino-TEMPO | 4-Amino-2,2,6,6-tetramethylpiperidine-1-oxyl, 4-Amino-2,2,6,6-tetramethylpiperidinyloxy, free radical (MW 171.26) | Sigma-Aldrich |
| DiR | 1,1'-Dioctadecyltetramethyl Indotricarbocyanine Iodide; near-infrared fluorophore | Caliper Lifesciences |
| 4T1 cells | Mouse mammary tumor cells | ATCC |
| PBS | Phosphate Buffered Saline | 1st Base, Singapore |
| DBU | 1,8-Diazabicyclo[5,4,0]undec-7-ene | Sigma-Aldrich |
| TMC | Trimethylene Carbonate | Sigma-Aldrich |
| Bis-MPA | 2,2-Dimethylol-Propionic Acid | Sigma-Aldrich |
| PFC | Bis-pentafluorophenyl carbonate | Iris Biotech GmbH |

Herein, Mn is the number average molecular weight, Mw is the weight average molecular weight, and MW is the molecular weight of one molecule.

$^1$H NMR spectra were acquired on a Bruker Avance 400 instrument at 400 MHz. Gel permeation chromatography (GPC) was performed in tetrahydrofuran (THF) using a Waters system equipped with four 5-micrometer Waters columns (300 mm×7.7 mm) connected in series with increasing pore size (100, 1000, 105, and 106 angstroms), a Waters 410 differential refractometer, and a 996 photodiode array detector. The system was calibrated using polystyrene standards. GPC analysis was also performed in N,N-dimethylformamide (DMF) spiked with 0.01 M LiBr using a Waters system equipped with two Agilent PolyPore columns (300 mm×7.5 mm) connected in series, a Waters 410 differential refractometer. The system was calibrated with poly(methyl methacrylate) standards.

Bis-pentafluorophenyl carbonate (PFC) was purchased from Iris Biotech GmbH (Marktredwitz, Germany) and purified by crystallizing twice from a mixture of ethyl acetate and hexanes.

N-bis(3,5-trifluoromethyl)phenyl-N'-cyclohexyl-thiourea (TU) has the following structure:

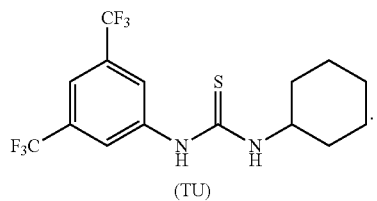

TU was prepared as reported by the method of R. C. Pratt, B. G. G. Lohmeijer, D. A. Long, P. N. P. Lundberg, A. Dove, H. Li, C. G. Wade, R. M. Waymouth, and J. L. Hedrick, Macromolecules, 2006, 39 (23), 7863-7871, and dried by stirring in dry THF over CaH$_2$, filtering, and removing solvent under vacuum.

Preparations of Cyclic Carbonates

Preparation of MTC-OH (MW 160.1).

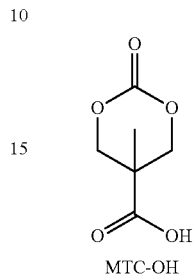

MTC-OH

MTC-OH can be prepared by the method of R. C. Pratt, et al., Chemical Communications, 2008, 114-116.

Preparation of MTC-OC6F5 (MW 326.2).

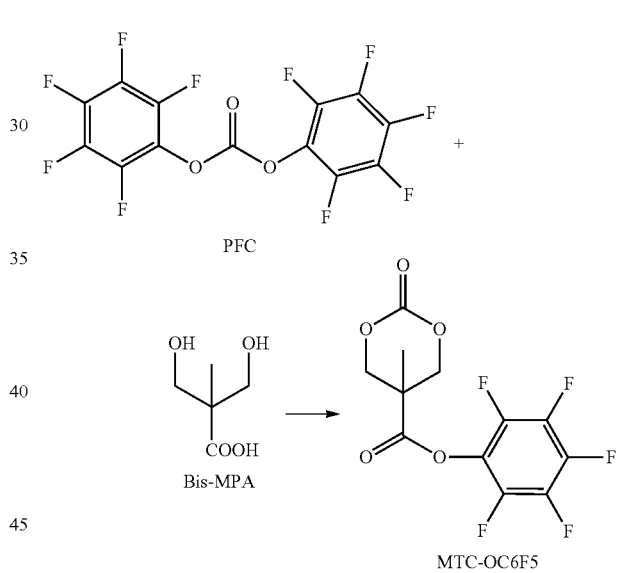

A 100 mL round bottom flask was charged with bis-MPA, (7), (5.00 g, 37 mmol, MW 134.1), bis-(pentafluorophenyl) carbonate (PFC, 31.00 g, 78 mmol, MW 394.1), and CsF (2.5 g, 16.4 mmol) rinsed with 70 mLs of tetrahydrofuran (THF). Initially the reaction was heterogeneous, but after one hour a clear homogeneous solution was formed that was allowed to stir for 20 hours. The solvent was removed in vacuo and the residue was re-dissolved in methylene chloride. The solution was allowed to stand for approximately 10 minutes, at which time the pentafluorophenol byproduct precipitated and could be quantitatively recovered. This pentafluorophenol byproduct showed the characteristic 3 peaks in the $^{19}$F NMR of pentafluorophenol and a single peak in the GCMS with a mass of 184. The filtrate was extracted with aqueous sodium bicarbonate and dried with MgSO$_4$. The solvent was evaporated in vacuo and the product was recrystallized (ethyl acetate/hexane mixture) to give MTC-OC6F5 as a white crystalline powder. The GCMS had a single peak with mass of 326 g/mol. The calculated molecular weight for $C_{12}H_7F_5O_5$ was consistent with the assigned structure. $^1$H-NMR (400 MHz in $CDCl_3$): delta 4.85 (d, J=10.8 Hz, 2H, $CH_aH_b$), 4.85 (d, J=10.8 Hz, 2H, $CH_aH_b$), 1.55 (s, 3H, $CCH_3$).

Synthesis of Polymers

Example 1

Preparation of active polymer AP-1, a diblock polymer comprising an MPEG5k block and a poly(MTC-OC6F5) block, 11 active carbonate units (x'=11). Square brackets in the AP-1 structure below indicate the blocks.

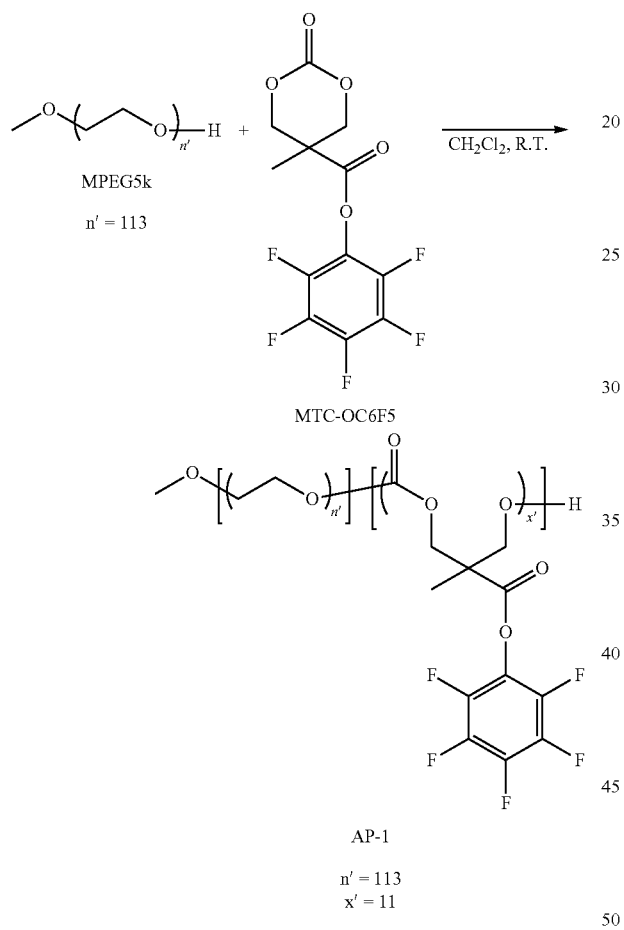

AP-1 n' = 113
x' = 11

In a nitrogen-purged glovebox, a small vial was charged with initiator MPEG5k (0.221 g, 0.0442 mmol, Mn=5000), active carbonate monomer MTC-OC6F5 (0.1875 g, 0.5749 mmol), and dichloromethane (0.47 g). The solution was stirred until the MPEG5k was fully dissolved. The MTC-OC6F5 is only partially soluble at this concentration. Finally, triflic acid (0.012 g, 0.080 mmol), an acid catalyst, was added to the stirred solution. As the reaction proceeded, the remaining MTC-OC6F5 slowly dissolved, giving a homogeneous solution. The reaction was monitored by $^1$H NMR. After stirring the reaction 70 hours at room temperature (r.t.), the polymer was precipitated into cold diethyl ether, isolated, and dried overnight under high vacuum to obtain a white solid (isolated yield: 0.180 g, 44%). $^1$H NMR ($CDCl_3$, 400 MHz): delta (ppm)=4.46 (s, 4H, carbonate C$\underline{H}_2$), 3.64 (s, 4H, OC$\underline{H_2CH_2}$), 1.51 (s, 3H, C$\underline{H}_3$). GPC (RI): Mn=11.3 kDa; PDI=1.10. DP of MTC-OC6F5 block (by $^1$H NMR end group analysis)=11.

Active polymer AP-1 is 41.8% polycarbonate (with pentafluorophenyl (PFP) ester) by mass. For the following reactions, if the mass of polymer weighed out is 1.0 g, the "relevant mass" for the substitution reaction is "0.42 g". The mmol value was calculated by dividing 0.42 by 326.17 (the molar mass of the MTC-OC6F5 repeat unit).

Example 2

Preparation of active polymer AP-2, a diblock polymer comprising an MPEG5k block and a poly(MTC-OC6F5) block, 8 active carbonate units (x'=8).

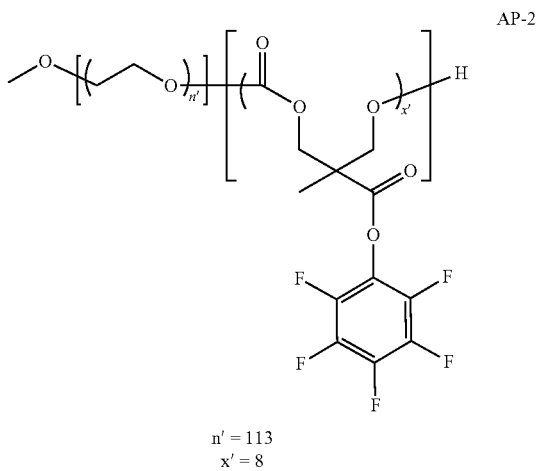

AP-2 n' = 113
x' = 8

AP-2 was prepared according to the general procedure of Example 1 using MPEG5k (2.36 g, 0.472 mmol, Mn=5000), MTC-OC6F5 (2.0 g, 6.13 mmol), dichloromethane (6.5 g), and triflic acid (0.140 g, 0.93 mmol). The isolated yield of polymer was 1.05 g. GPC produced a monomodal peak with a calculated Mn=10198, Mw 12624; PDI=1.24. DP of MTC-OC6F5 block (by $^1$H NMR end group analysis)=8.

Example 3

Preparation of radical polymer P1-11, 11 PROXYL units (m'=11).

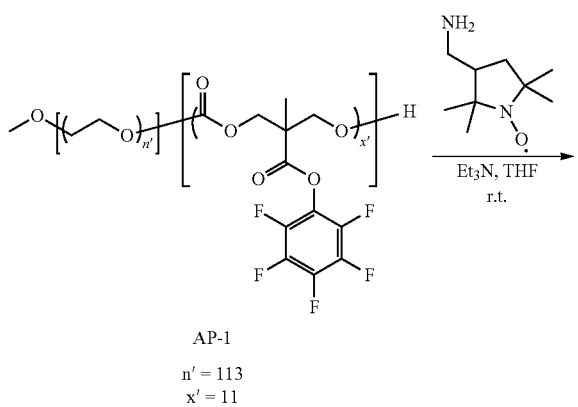

AP-1 n' = 113
x' = 11

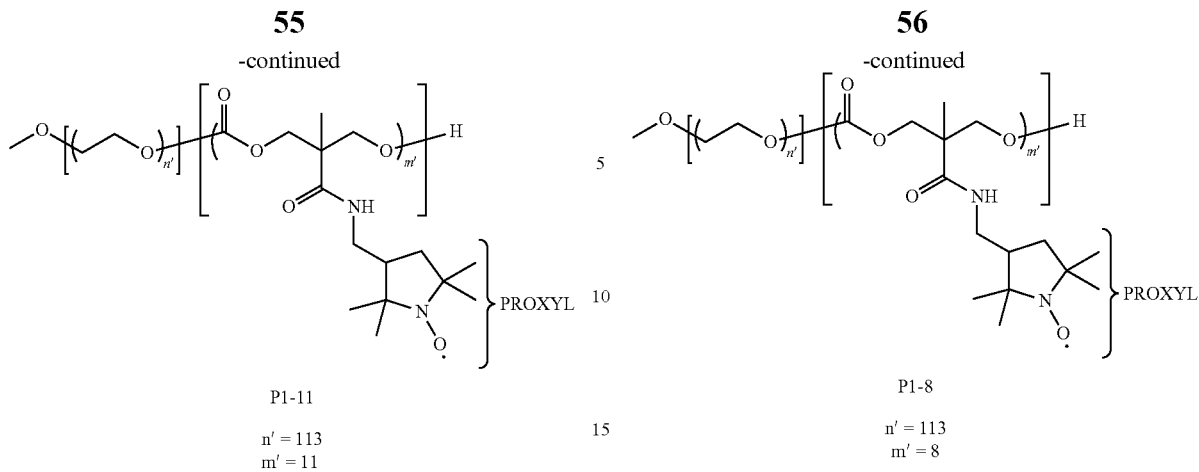

P1-11 n' = 113
m' = 11

A 4-mL glass vial containing a magnetic stir-bar was charged with active polymer AP-1 (0.180 g, 0.231 mmol of pentafluorophenyl ester groups, n'=113), anhydrous THF (2.0 mL), and triethylamine (0.0260 g, 0.254 mmol). A solution of 3-(aminomethyl)-PROXYL (0.0434 g, 0.254 mmol) in THF (0.5 mL) was added with stirring. The mixture was allowed to stir for 45 minutes at room temperature (r.t.), after which it was pipetted into excess diethyl ether (16 mL) to precipitate the polymer as an off-white solid. The mixture was briefly sonicated and then centrifuged. The mother liquor was decanted off and more diethyl ether (20 mL) was added. A second round of sonication, centrifuging, and decanting afforded an off-white solid that was then dried under high vacuum for 24 hours (isolated yield: 0.175 g, 99%). GPC (THF): Mn=9176, PDI=1.23.

The polycarbonate block of P1-11 has a terminal hydroxy group (i.e., P1-11 was not end-capped). No meaningful NMR spectra could be obtained with the paramagnetic radical-containing polymers due to severe line-broadening.

Example 4

Preparation of radical polymer P1-8, 8 PROXYL units, (m'=8).

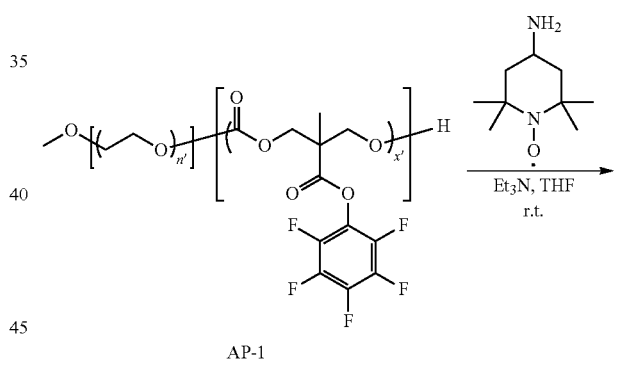

AP-2 n' = 113
x' = 8

P1-8 n' = 113
m' = 8

P1-8 was prepared using the general procedure of Example 3 and AP-2 (0.150 g, 0.158 mmol of pentafluorophenyl ester groups, n'=113), anhydrous THF (2 mL), triethylamine (0.016 g, 0.158 mmol, 1 eq.), and a solution of 3-(aminomethyl)-PROXYL (0.030 g, 0.173 mmol, 1.1 eq.) in THF (2 mL). The isolated yield was 0.123 g. GPC characterization resulted in a single monomodal peak with a calculated Mw=10351, Mn=8888, and PDI of 1.16.

Example 5

Preparation of Radical Polymer P2-11, 11 TEMPO Units (m'=11)

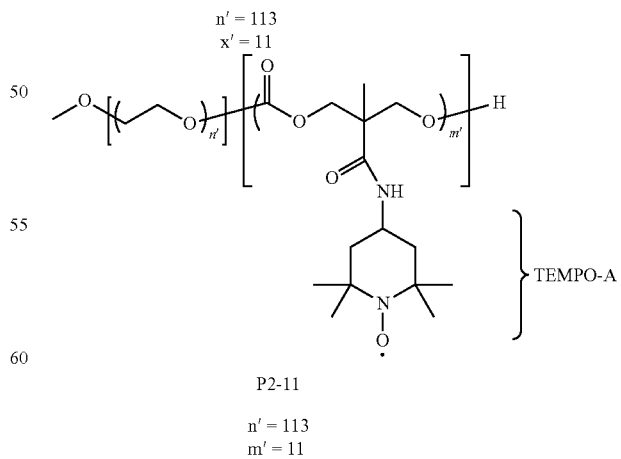

AP-1 n' = 113
x' = 11

P2-11 n' = 113
m' = 11

A 4-mL glass vial containing a magnetic stir-bar was charged with active polymer AP-1 (0.300 g, 0.384 mmol of pentafluorophenyl ester groups), anhydrous THF (2.0 mL) and triethylamine (0.0390 g, 0.385 mmol). A solution of 4-amino-TEMPO (0.0790 g, 0.461 mmol, 1.2 equivalents) in THF (1.0 mL) was added with stirring. The mixture was allowed to stir for 45 minutes at room temperature, after which it was pipetted into excess diethyl ether (16 mL) to precipitate the polymer as an off-white solid. The mixture was briefly sonicated and then centrifuged. The mother liquor was decanted off and more diethyl ether (20 mL) was added. A second round of sonication, centrifuging, and decanting afforded an off-white solid that was dried under high vacuum for 24 hours (isolated yield: 0.292 g, 99%). GPC (THF): Mn=8956, PDI=1.19.

The polycarbonate block of P2-11 has a terminal hydroxy group (i.e., P2-11 was not end-capped).

Example 6

Preparation of radical polymer P2-8, 8 TEMPO-A units (m'=8).

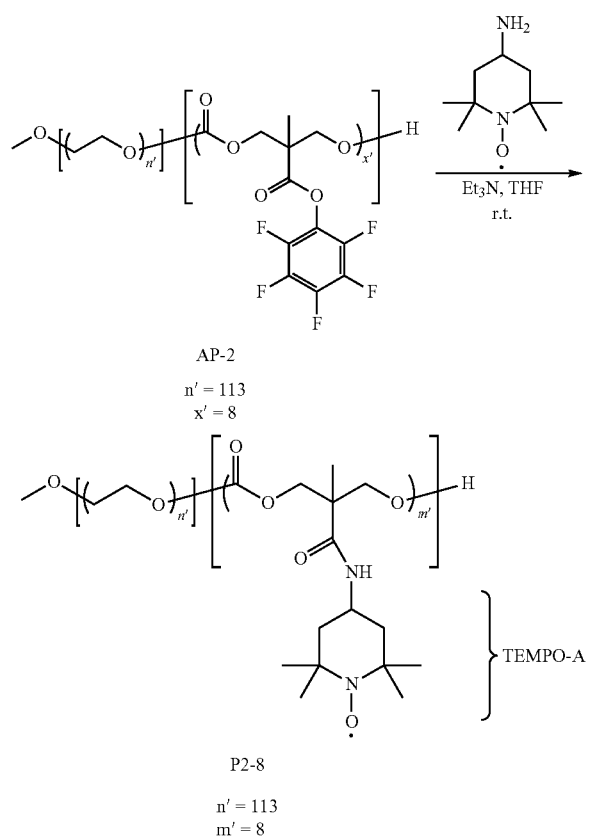

P2-8 was prepared using the general procedure of Example 5 and AP-2 (0.150 g, 0.158 mmol of pentafluorophenyl ester groups), anhydrous THF (2 mL), triethylamine (0.016 g, 0.158 mmol), and a solution of 4-amino-TEMPO (0.030 g, 0.175 mmol, 1.1 equivalents) in THF (2 mL). The isolated yield was 0.141 g. GPC (THF): Mn=9327, Mw=11407 PDI=1.22.

Table 2 summarizes the preparation of the radical polymers. PDI=polydispersity index.

TABLE 2

| Example | Name | PEG block DP (n') | Polycarbonate block DP (m') | Radical Moiety | Mn | PDI |
|---|---|---|---|---|---|---|
| 3 | P1-11 | 113 | 11 | PROXYL | 9176 | 1.23 |
| 4 | P1-8 | 113 | 8 | PROXYL | 8888 | 1.16 |
| 5 | P2-11 | 113 | 11 | TEMPO-A | 8956 | 1.19 |
| 6 | P2-8 | 113 | 8 | TEMPO-A | 9327 | 1.22 |

Relaxation time $T_1$ measurements

The spin-active block polymers were capable of reducing the measured $T_1$ value of a phosphate buffered saline solution (with 5% by volume D20), providing examples of TEMPO and PROXYL containing polymers that exhibit the same behavior. The narrow polydispersities of these polymers (PDI=ca. 1.2) enables a reliable approximation of radical concentration for a given mass of polymer. A graph of $T_1$ values vs. calculated radical concentrations exhibits a strong linear relationship ($R^2 > 0.99$) consistent with other reported MRI contrast agents.

All experiments were carried out on a Bruker 300 MHz NMR using a saturation recovery pulse program. A total of nine $T_1$ measurements were carried out in a phosphate-buffered saline solution with 5% by volume D20 at varying concentrations of spin-active polymer component.

Relaxation time $T_1$ measurements were initially conducted on polymer P1-11 having 11 PROXYL radicals. To ensure that the relaxation of water was being reduced by the spin-active PROXYL moieties of the polymer, a control was performed using the MPEG5k starting material, Mn 5000. In this control, $T_1$ was measured as a function of increasing polymer concentration. A total of five $T_1$ measurements were conducted with this control. Table 3 summarizes the polymer concentrations used for the $T_1$ measurements for P1-11 and control polymer MPEG5k.

TABLE 3

| | Spin-Active Polymer P1-11 | | | MPEG5k Control | |
|---|---|---|---|---|---|
| | | Calculated | | | |
| Titration Number | Amount (mg) | Polymer Concentration (Mm) | Radical Concentration (Mm) | Amount (Mg) | Polymer Concentration (Mm) |
| 1 | 0 | 0 | 0 | 0 | 0 |
| 2 | 2.2 | 0.29 | 2.34 | 1.6 | 0.32 |
| 3 | 4.0 | 0.53 | 4.26 | 4.0 | 0.80 |
| 4 | 5.8 | 0.77 | 6.18 | 6.5 | 1.30 |
| 5 | 8.8 | 1.17 | 9.38 | 10.5 | 2.10 |
| 6 | 10.3 | 1.37 | 11.0 | 16.3 | 3.26 |
| 7 | 12.1 | 1.61 | 12.9 | | |
| 8 | 14.7 | 1.96 | 15.7 | | |
| 9 | 17.0 | 2.26 | 18.1 | | |
| 10 | 20.0 | 2.66 | 21.3 | | |

Using a saturation recovery pulse program several $^1$H NMR spectra were taken with increasing pulse lengths (FIG. 1, overlaid spectra). The dominant water peak was integrated at each interval and plotted against the respective pulse length. The equation describing the function relating the saturation recovery method to $T_1$ values is:

$$M_{xy}(t) = M_o(1 - e^{-TR/T_1})$$

where $M_{xy}$ is the transverse magnetization, $M_o$ is the equilibrium longitudinal magnetization, and TR is the time interval of the applied pulses.

Figure 2:
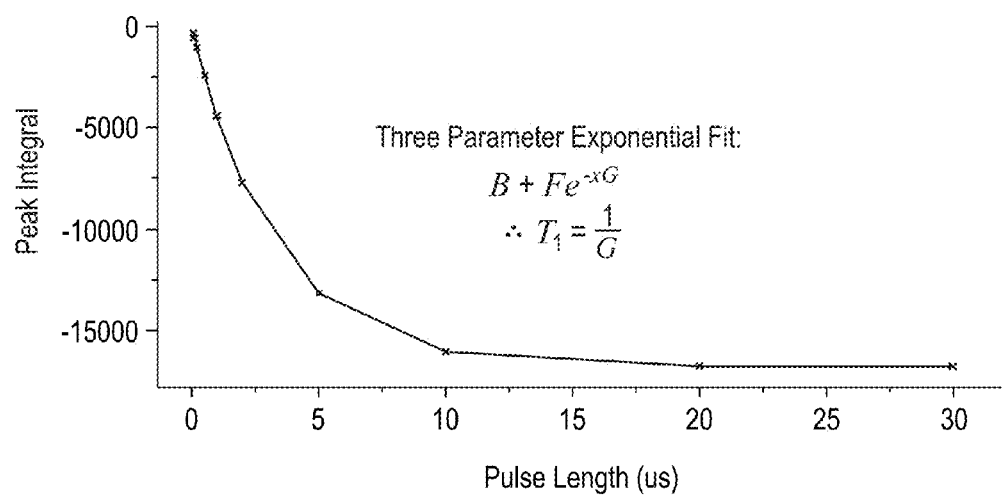
FIG. 2 is a graph of $^1$H NMR peak integrals versus pulse length (crosses) along with solid line showing the fitted model of the form of a three parameter exponential fit for radical polymer P1-11. The $T_1$ values can be calculated from the fitting parameter G.

The data points were fitted to a three-parameter exponential fit where the fitting parameter G can be utilized to calculate the $T_1$ values. The experimental data fitted well using this model. FIG. 2 is a graph of peak integrals versus pulse length (crosses) along with a solid line showing the fitted model of the form of a three parameter exponential fit. The $T_1$ values can be calculated from the fitting parameter G. Typical mean squared error values were <0.0007. $T_1$ values were generated for each polymer concentration.

$T_1$ Results

Figure 3:
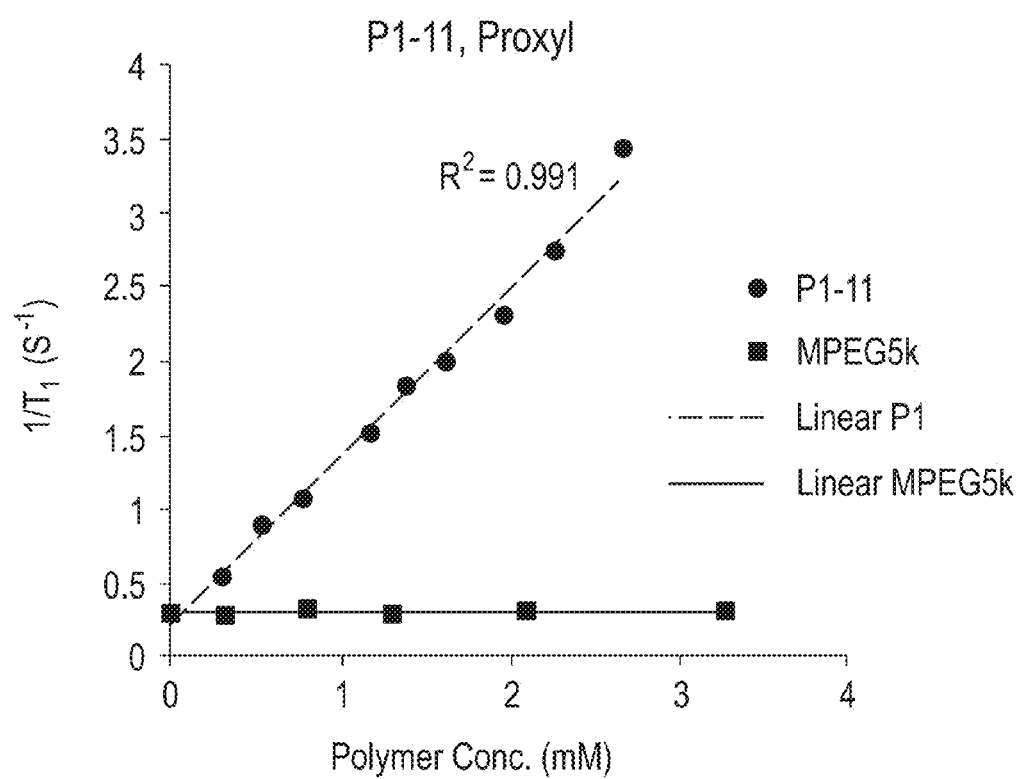
FIG. 3 is a graph of $1/T_1$ values versus concentration of polymer P1-11 and a MPEG5k control.
Figure 4:
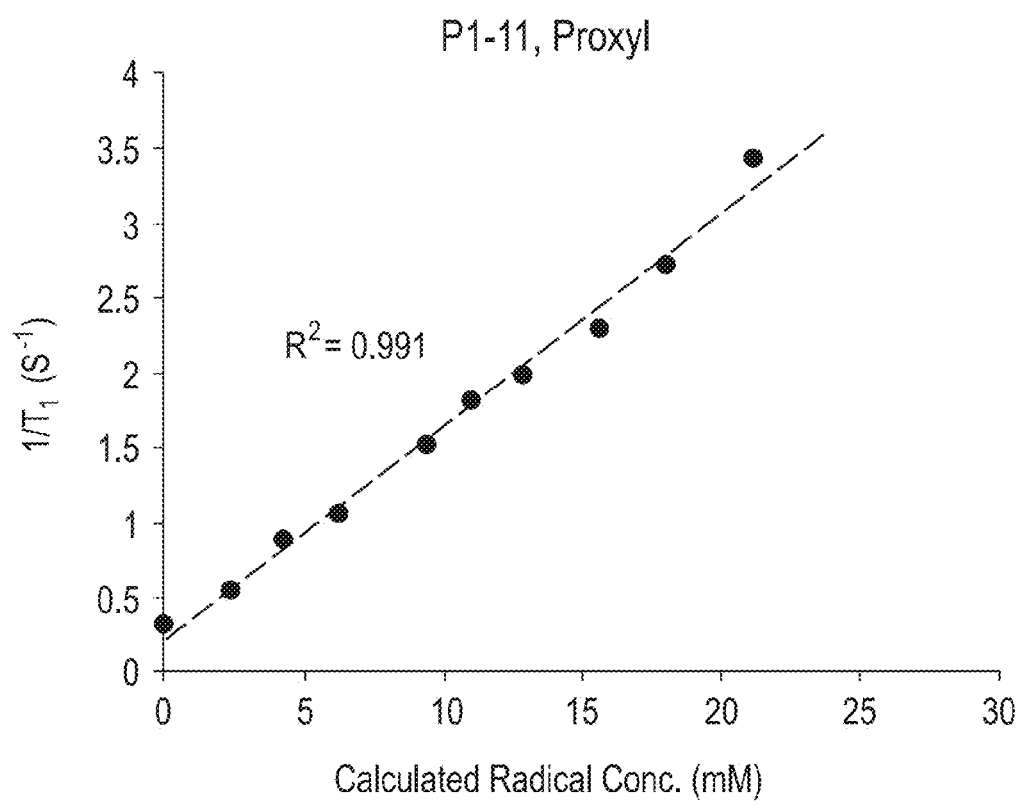
FIG. 4 is a graph of $1/T_1$ values versus calculated radical concentration for P1-11.

The spin-active polymer P1-11 was capable of reducing the measured $T_1$ value of a phosphate buffered saline (PBS) solution (with 5% by volume $D_2O$, $T_1$=3.26 seconds) by an order of magnitude at a polymer concentration as low as 2.7 mM ($T_1$=0.29 seconds). To demonstrate that the PROXYL moieties of this block copolymer are responsible for the significant reductions in $T_1$, a control study was performed using varying concentrations of MPEG5k (FIG. 3). As the concentration of MPEG5k is increased, no significant decrease in $T_1$ is observed. In addition, the narrow polydispersity (PDI≈1.2) of P1-11 enables a reliable approximation of radical concentration for a given mass of polymer. FIG. 4 is a graph of $T_1$ values versus calculated radical concentrations for P1-11. A strong linear relationship ($R^2$>0.99) consistent with other reported MRI contrast agents was obtained.

Based on these observations the PROXYL-containing block copolymer P1-11 is capable of supplying a high concentration of an active relaxation agent at a low polymer concentration. This property enables the polymer to significantly reduce the $T_1$ of a PBS solution suggesting this material could be implemented as a magnetic resonance image (MRI) contrast agent. Furthermore, the biocompatibility of the polymer design will enable higher loadings in vivo to achieve higher contrast and shorter $T_1$ values.

Figure 5:
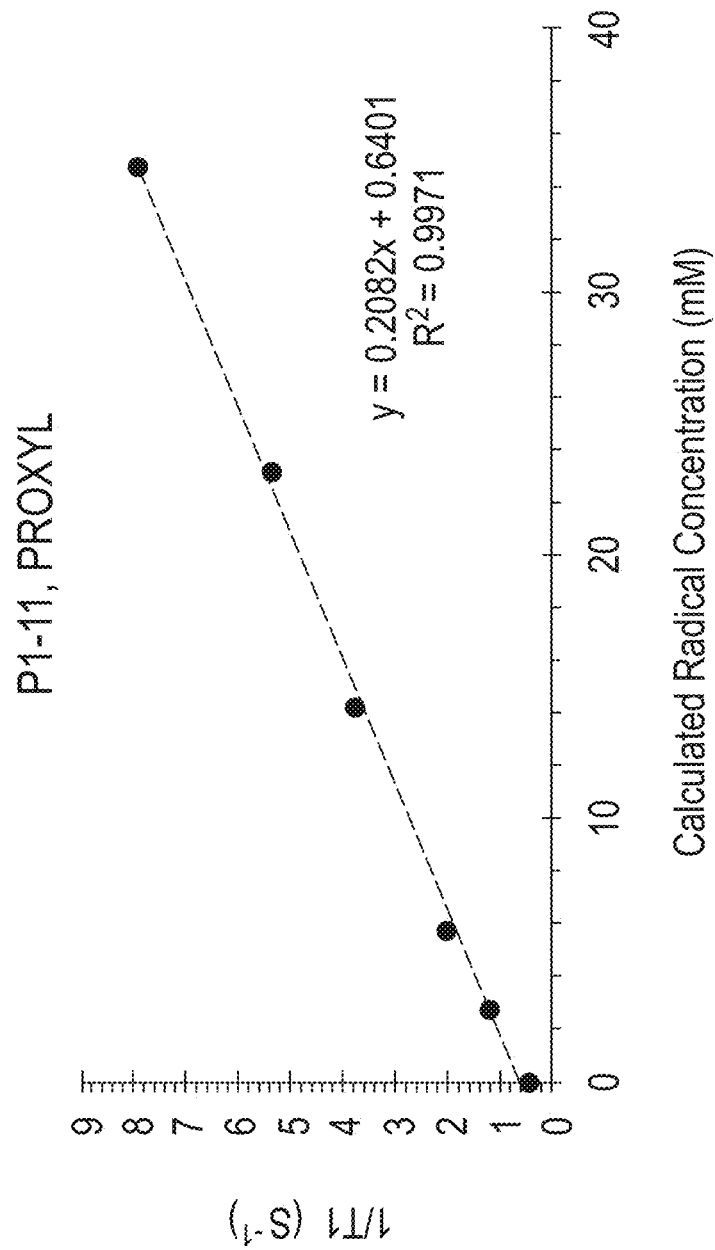
FIG. 5 is a graph of $1/T_1$ values versus calculated radical concentration for P1-11 for comparison with FIG. 6.
Figure 6:
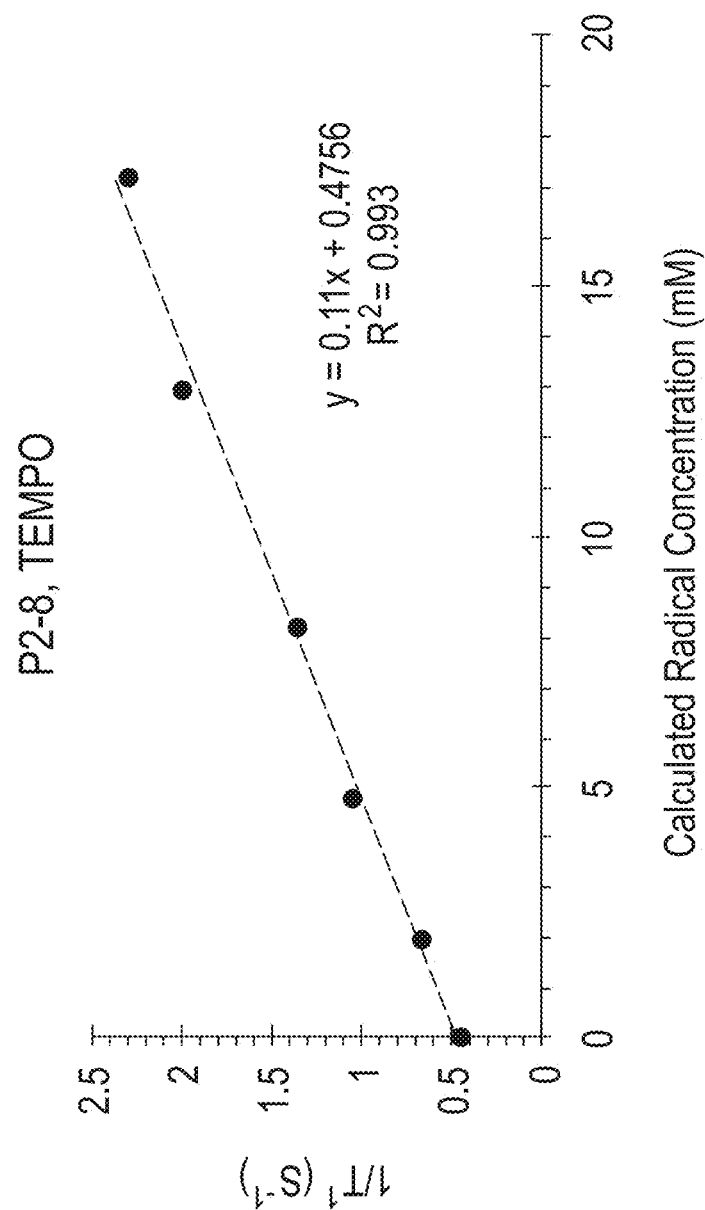
FIG. 6 is a graph of $1/T_1$ values versus calculated radical concentration for P2-8 (8 TEMPO-A units).

FIG. 5 and FIG. 6 are graphs of $T_1$ values versus calculated radical concentration for P1-11 and P2-8, respectively. A comparison of these different polymers indicates that the presence of a higher number of spin active components (11 versus 8, respectively) relaxes the surrounding environment more efficiently. This efficiency is described through a quantity, relaxivity, that can be calculated using the data points of FIG. 5 and FIG. 6 to calculate a linear fit, where the slope of the linear relationship is the measured relaxivity. In the case of a P1-8 (8 PROXYL units) the relaxivity was 0.14 $mM^{-1}S^{-1}$ at 7.00 T. In the case of P2-8 (8 TEMPO-A units) having the same number of spin-active units, the relaxivity was slightly less, 0.11 $mM^{-1}S^{-1}$ at 7.00 T, indicating that the PROXYL moiety was more efficient at relaxation compared to TEMPO. When the number of PROXYL units was increased from 8 (P1-8) to 11 (P1-11) the relaxivity increased from 0.14 to 0.21 $mM^{-1}S^{-1}$ at 7.00 T, respectively.

Although each of the PROXYL polymers appeared to be fully soluble in the aqueous solution used in this experiment, solutions of the TEMPO polymer P2-11 were turbid, suggesting incomplete solubility or the formation of macroscopic aggregates under these conditions.

Preparation of P1-11 Nanoparticles

Polymer P1-11 (10 mg) was dissolved in N,N-dimethylformamide (DMF, 2 mL) and transferred to a dialysis membrane tube with molecular weight cut-off (MWCO) of 1000 Da (Spectrum Laboratories, U.S.A.). The dialysis bag was immersed in de-ionized water (DI, 1 liter) at 4° C. for 2 days. The dialysis medium was replaced at 3rd, 6th and 24th hour with fresh DI water. At the end of the dialysis process, the resulting micelle solution was centrifuged at 4000 rpm for 5 minutes to remove large aggregates if present.

Using the dialysis technique, P1-11 was able to self-assemble into nanoparticles of size 103±2 nm, PDI 0.45±0.01. Polymer P2-11 was found to be insoluble in water and hence in vivo biodistribution experiments were conducted using only P1-11.

DiR-Loaded Nanoparticles

Noninvasive near-infrared fluorescence (NIRF) imaging was used to monitor the real-time in vivo biodistribution of the nanoparticles. NIRF dyes have less interference from background fluorescence due to the minimal absorption of near-infrared (NIR) photons by water or hemoglobin. In this study, a NIRF dye DiR was used as a model compound for encapsulation into the P1-11 nanoparticles (2.9 wt % DiR).

DiR was loaded into the nanoparticles during nanoparticle formation via dialysis. P1-11 (10 mg) and DiR (1 mg) were dissolved in 2 mL of N,N-dimethylformamide (DMF) and dialysed against de-ionized (DI) water at 4° C. for 2 days. To determine the loading level of DiR, the nanoparticles of dye-loaded P1-11 were lyophilized and re-dissolved in DMSO. The light absorbance was measured against a standard calibration curve of free dye dissolved in DMSO at 759 nm wavelength.

Biodistribution of Nanoparticles

Animal studies were carried out as follows: Balb/c mice, weighing 20-30 g, were injected subcutaneously with 200 microliters of a cell suspension containing $0.5 \times 10^6$ 4 T1 cells. After 2 weeks, when the tumors reached 4-6 mm in diameter, the mice were administered with the DiR-loaded P1-11 nanoparticles at 4.5 mg/kg via tail vein injection. Non-invasive fluorescent imaging was performed at various times up to 7 days after the injection using an IVIS 100 instrument (Caliper Life Sciences, U.S.A.). Anesthetized animals were placed on an animal plate heated to 37° C. The near-infrared fluorescence was imaged using the indocyanine green (ICG) filter pairs and exposure time was set to 3 seconds and 1 second for live animals and organs, respectively. Scans were performed at 5 minutes, 1 hour, 6 hours, 24 hours, 48 hours, 4 days, and 7 days post-intravenous administration. On day 7, the mice were sacrificed and organs were resected to estimate the biodistribution of nanoparticles in various tissues (tumors, heart, liver, spleen, lungs and kidneys).

Biodistribution Results

Figure 7:
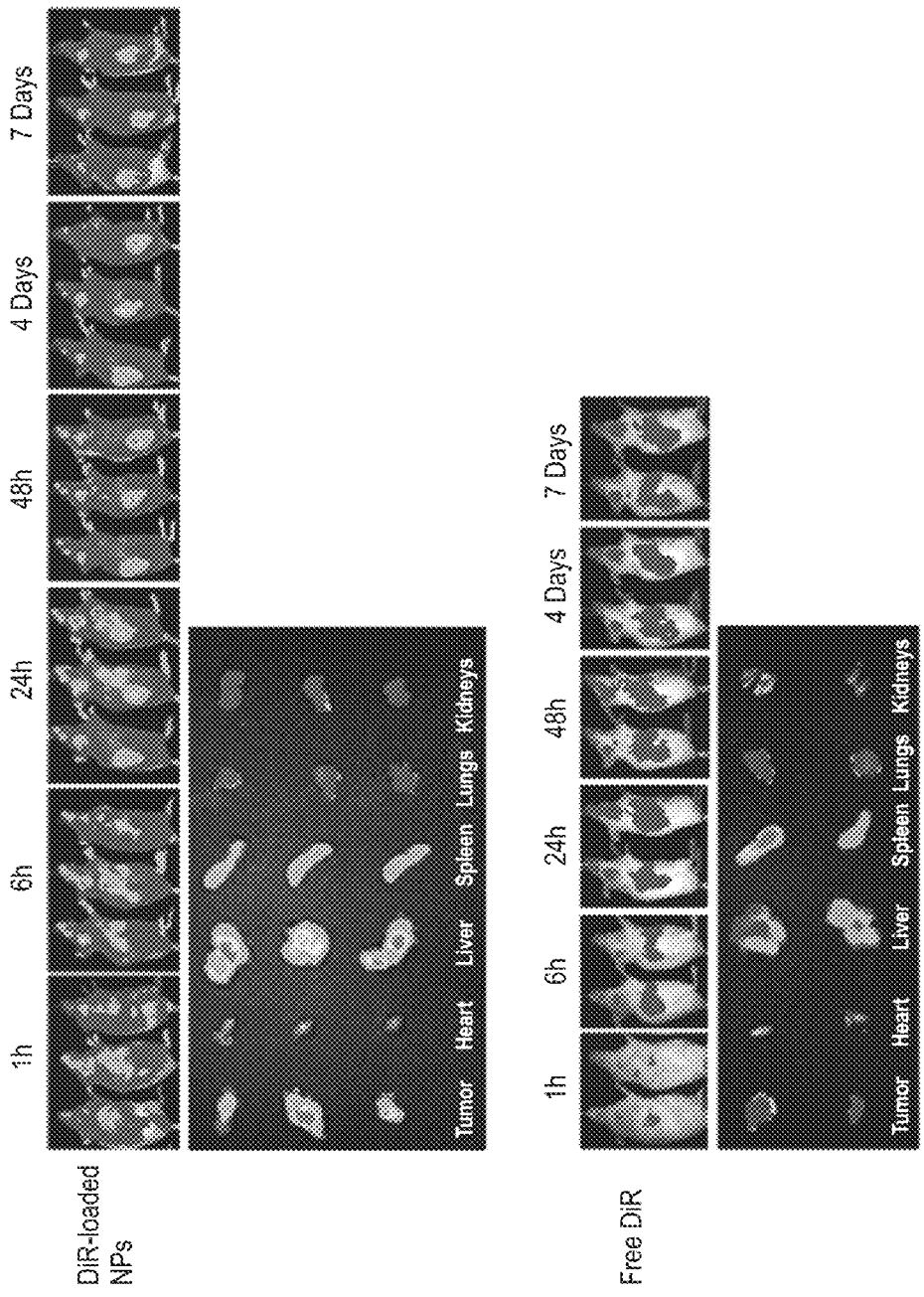
FIG. 7 is a series of non-invasive near-infrared fluorescence (NIRF) images of 4T1 (mouse breast cancer line) tumor-bearing mice following intravenous administration of DiR-loaded P1-11 nanoparticles versus free DiR of various organs at 7 days post intravenous administration.

By 1 hour post injection, the DiR-loaded nanoparticles were distributed throughout the animals. Appreciable contrast between subcutaneous tumor and normal tissues was observed from 24 hours post injection onwards (FIG. 7, series of mouse images). This passive tumor targeting ability of P1-11 nanoparticles could be attributed to the extended circulation time of the nanoparticles and the enhanced permeability and retention (EPR) effect occurring within the tumor tissue, which can increase the accumulation of the nanoparticles in the tumor tissue.

On day 7 post injection, the mice were sacrificed and major organs as well as the tumor were resected to evaluate the tissue distribution of DiR-loaded nanoparticles. From the images obtained, higher NIRF intensity was observed from the tumors of mice injected with the nanoparticles as compared to those injected with free DiR. This provides strong indication that the fluorescence emission from the tumor occurs as a result of the accumulation of nanoparticles via passive targeting effects. In mice treated with DiR-loaded nanoparticles, NIRF intensities were generally lower for normal tissues compared to the tumor and in particular, negligible fluorescence signal was detected from the heart. This targeted positioning of the nanoparticles into tumors can potentially translate to usage as an indicator for monitoring tumor location and progression.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A polymer comprising:

a radical repeat unit having a structure according to formula (1):

(1)

wherein

R' is monovalent group selected from the group consisting of hydrogen (H—*) and groups comprising 1-5 carbons, each R" is an independent monovalent group selected from the group consisting of hydrogen (H—*) and methyl (Me-*), and W' is a monovalent moiety comprising a nitroxide radical selected from the group consisting of (TEMPO-A) (TEMPO-B) , and (PROXYL)

2. The polymer of claim 1, wherein the nitroxide radical is (TEMPO-A)

3. The polymer of claim 1, wherein the nitroxide radical is (TEMPO-B)

4. The polymer of claim 1, wherein the nitroxide radical is (PROXYL)

5. The polymer of claim 1, wherein each R" is hydrogen (H—*).

6. The polymer of claim 1, wherein W' is selected from the group consisting of

-continued

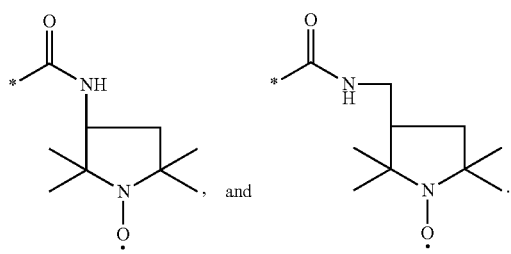

7. The polymer of claim 1, wherein the radical repeat unit is selected from the group consisting of

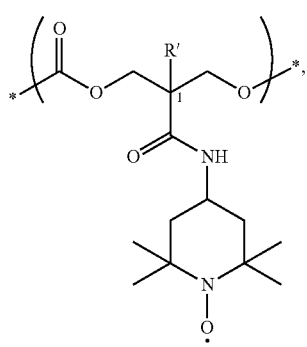

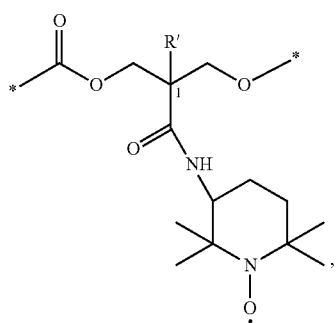

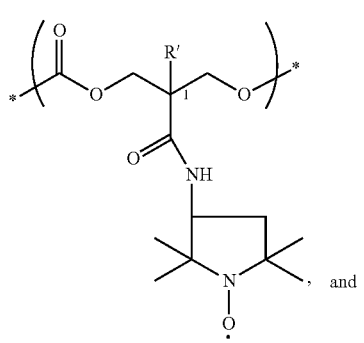
and

-continued

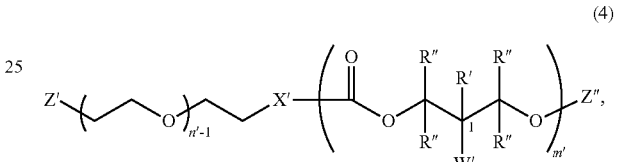

wherein R' is monovalent group selected from the group consisting of hydrogen (H—*) and groups comprising 1-5 carbons.

8. A block polymer of formula (4):

$$Z'\underbrace{\left(\phantom{\frac{}{}}\!\!\!\!-\!\!-\!\text{O}\!-\!\!\!\!\phantom{\frac{}{}}\right)_{n'-1}}\!\!X'\!\!-\!\!\left(\!\!\begin{array}{c}\text{O}\\\|\\\text{C}\end{array}\!\!-\!\!\text{O}\!-\!\!\begin{array}{c}R''\\|\\R''\end{array}\!\!\!\!\begin{array}{c}R'\\|\\W'\end{array}\!\!\!\!\begin{array}{c}R''\\|\\R''\end{array}\!\!\!\!-\!\!\text{O}\!\!\right)_{m'}\!\!\!Z'',\tag{4}$$

wherein
n' represents the number of ethylene oxide repeat units, and has an average value of about 10 to about 250,
m' represents the number of radical repeat units, and has an average value of 1 to about 100,
each R' is an independent monovalent moiety selected from the group consisting of hydrogen (H—*) and groups comprising 1 to 5 carbons,
each R″ is an independent monovalent moiety selected from the group consisting of hydrogen (H—*) and methyl (Me-*),
X' is a divalent linking group selected from the group consisting of oxygen (*—O—*), *—N(H)—*, and sulfur (*—S—*),
each W' is a monovalent moiety comprising a nitroxide radical selected from the group consisting of (TEMPO-A)

(TEMPO-B)

and

-continued (PROXYL)

each Z' is a monovalent first end group selected from the group consisting of hydrogen (H—*) and groups comprising 1 or more carbons, and each Z" is a monovalent second end group selected from the group consisting of hydrogen (H—*) and groups comprising 1 or more carbons.

9. The block polymer of claim 8, wherein n' has an average value of about 50 to about 200, and m' has an average value of about 1 to about 20.

10. The block polymer of claim 8, wherein Z' is an alkoxy or aryloxy group comprising 1 to 15 carbons, X' is oxygen (*—O—*), and Z" is hydrogen (H—*).

11. A composition, comprising:
water; and
the block polymer of claim 8;
wherein
the composition is suitable for enhancing contrast in a medical imaging application.

12. The composition of claim 11, wherein the composition comprises micelles of the block polymer.

13. The composition of claim 11, wherein the composition is suitable for intravenous injection.

14. The composition of claim 11, wherein the composition further comprises a drug.

15. The composition of claim 11, wherein the composition further comprises a contrast enhancing dye.

16. The composition of claim 15, wherein the contrast enhancing dye fluoresces at a wavelength in the range of about 700 nm to about 900 nm.

17. A method, comprising:
forming a first mixture comprising water and the block polymer of claim 8;
forming a second mixture comprising i) a solvent selected from the group consisting of organic solvents, water, and combinations thereof and ii) a medically useful material;
combining the first mixture and the second mixture, thereby forming a third mixture; and
removing organic solvent from the third mixture, thereby forming a composition comprising particles, the particles comprising the block polymer and the medically useful material bound by non-covalent interactions.

18. The method of claim 17, wherein the medically useful material is a contrast enhancing dye suitable for a medical imaging application.

19. The method of claim 18, wherein the medical imaging application is magnetic resonance imaging.

20. The method of claim 17, wherein the medically useful material is a drug.

21. The method of claim 17, wherein an aqueous mixture of the particles is suitable for intravenous injection.

22. A method, comprising:
contacting living tissue with the polymer of claim 1, thereby enhancing contrast in a medical imaging application used to view the tissue and/or administering a therapeutic treatment to the tissue, wherein the polymer is water soluble, non-toxic, biodegradable, and paramagnetic.

23. The method of claim 22, wherein the polymer is a block polymer of formula (4):

$$Z'\left(\!\!\begin{array}{c}\\O\end{array}\!\!\right)_{n'-1}\!\!\!X'\!\!\left(\!\!\begin{array}{c}O\\\|\\C\end{array}\!\!-\!\!O\!\!-\!\!\begin{array}{c}R''\\|\\R''\end{array}\!\!\begin{array}{c}R'\\|\\\underset{W'}{|}\end{array}\!\!\begin{array}{c}R''\\|\\R''\end{array}\!\!-\!\!O\!\!\right)_{m'}\!\!\!Z'', \quad (4)$$

wherein
n' represents the number of ethylene oxide repeat units, and has an average value of about 10 to about 250,
m' represents the number of radical repeat units, and has an average value of 1 to about 100,
each R' is an independent monovalent moiety selected from the group consisting of hydrogen (H—*) and groups comprising 1 to 5 carbons,
each R" is an independent monovalent moiety selected from the group consisting of hydrogen (H—*) and methyl (Me-*),
X' is a divalent linking group selected from the group consisting of oxygen (*—O—*), *—N(H)—*, and sulfur (*—S—*),
each W' is a monovalent moiety comprising a nitroxide radical selected from the group consisting of (TEMPO-A)   (TEMPO-B)   and (PROXYL)

each Z' is a monovalent first end group selected from the group consisting of hydrogen (H—*) and groups comprising 1 or more carbons, and each Z" is a monovalent second end group selected from the group consisting of hydrogen (H—*) and groups comprising 1 or more carbons.

24. The method of claim 22, wherein the polymer is administered to a medical patient.

25. The method of claim 22, wherein said contacting living tissue with the polymer enhances contrast in a medical imaging application used to view the tissue.

26. The method of claim 25, wherein the polymer is bound by non-covalent interactions to a near infrared fluorescent (NIRF) dye.

27. The method of claim 26, wherein the NIRF dye is 1,1'-dioctadecyltetramethyl indotricarbocyanine iodide (DiR).

28. The method of claim 22, wherein said contacting living tissue with the polymer administers a therapeutic treatment to the tissue.

* * * * *